United States Patent [19]

Löbberding et al.

[11] Patent Number: 5,849,893
[45] Date of Patent: Dec. 15, 1998

[54] NUCLEIC ACID-BINDING OLIGOMERS POSSESSING C-BRANCHING FOR THERAPY AND DIAGNOSTICS

[75] Inventors: Antonius Löbberding, Wuppertal; Burkhard Mielke, Leverkusen; Christoph Schwemler, Leichlingen; Eckhard Schwenner, Wuppertal; Udo Stropp, Haan; Wolfgang Springer, Wuppertal; Axel Kretschmer, Bergisch Gladbach; Thorsten Pötter, Köln, all of Germany

[73] Assignee: Bayer Aktiengesellschaft, Leverkusen, Germany

[21] Appl. No.: 719,048

[22] Filed: Sep. 24, 1996

Related U.S. Application Data

[62] Division of Ser. No. 300,910, Sep. 6, 1994.

[30] Foreign Application Priority Data

Sep. 13, 1993 [DE] Germany .......................... 43 31 011.7

[51] Int. Cl.$^6$ .................................................. C07H 21/04
[52] U.S. Cl. .......................................... 536/23.1; 530/300
[58] Field of Search ............................. 530/300; 536/23.1

[56] References Cited

U.S. PATENT DOCUMENTS

| | | | |
|---|---|---|---|
| 5,142,047 | 8/1992 | Summerton et al. | 544/118 |
| 5,539,082 | 7/1996 | Nielsen et al. | 530/300 |

FOREIGN PATENT DOCUMENTS

| | | |
|---|---|---|
| 0300796 | 1/1989 | European Pat. Off. . |
| WO9220702 | 11/1992 | WIPO . |
| WO9220703 | 11/1992 | WIPO . |
| WO9304701 | 3/1993 | WIPO . |

OTHER PUBLICATIONS

Buttrey et al., Tetrahedron vol. 31, pp. 73–75, 1975.
Antiviral Chemistry & Chemotherapy, 1991, vol. 2, No. 4, pp. 191–214; "Towards gene–inhibition therapy: a review of progress . . . ", W. James.
Tibtech, May, 1992, vol. 10, pp. 152–158; "Antisense oligonucleotides as antiviral agents", S. Agrawal.
Cancer Research, vol. 51, pp. 4505–4510, Sep. 1, 1991; "Inhibition of Protooncogene Expression by Antisense Oligodeoxynucleotides . . . ", B. Calabretta.
Anti–Cancer Drug Design, 1991, vol. 6, pp. 569–584; "The anti–gene strategy: control of gene expression by triplex–forming . . . ", C. Hélène.
Chemical Reviews, vol. 90, No. 4, Jun. 1990, cover page + 544–584; "Antisense oligonucleotides: a new therepeutic principle", E. Uhlmann et al.

The Journal of Organic Chemistry, vol. 33, No. 4, Apr. 1968; "N–vinyl derivatives of substituted pyrimidines and purines", J. Pitha et al.
Advances in Polymer Science 50, Springer–Verlag Berlin Hiedelberg, 1983, pp. 1–16; "Physiological activities of synthetic analogs of . . . ", J. Pitha; vol. 50.
Principles of peptide synthesis, M. Bodanszky, Springer–Verlag, 3 pages.
Tetrahedron Letters, vol. 34, No. 8, pp. 1275–1278, 1993; "Peptide–based nucleic acid surrogates incorporating Ser [CH$_2$B]–Gly", P. Garner et al.
Tetrahedron Letters, vol. 32, No. 50, pp. 7385–7388, 1991; "Solid phase synthesis of neutral oligonucleotide analogues", H. Wang et al.
The Journal of Organic Chemistry, 1991, vol. 56, pp. 6007–6018; "Acyclic nucleic acid analogues: synthesis and oligomerization . . . ", S.B. Huang et al.
Journal of Molecular Evolution, 1990, vol. 30, pp. 315–321; "Polymerization of amino acids containing nucleotide bases", A.B. Cheikh et al.
Rec. Trav. Chim., vol. 91, 1972, pp. 1069–1078; "The reduction of alkyl–naphthalenes with lithium in liquid ammonia", Th.J. Nieuwstad et al.
Chemical Abstracts, vol. 113, Nov. 19, 1990, No. 21, pp. 1/776; CA# 191856t: "Preparation of oligodeoxyribonucleotide–based . . . ", p. Westermann et al.
Chemical Abstracts, vol. 94, Feb. 2, 1981, No. 5, pp. 1/185; CA# 26354j: "Specific interaction between oligovaline and . . . ", S.A. Strel'tsov et al.
Zhurnal Obshchei Khimii, vol. 57, No. 6, pp. 1393–1401, Jun. 1987; "Nucleo acids and nucleopeptides", G.A. Korshunova et al.
Garner et al, Tetrahedron Letters 34: 1275–1278.

*Primary Examiner*—Scott W. Houtteman
*Attorney, Agent, or Firm*—Sprung Kramer Schaefer & Briscoe

[57] ABSTRACT

The invention relates to nucleic acid-binding oligomers possessing C-branching of the general formula (I)

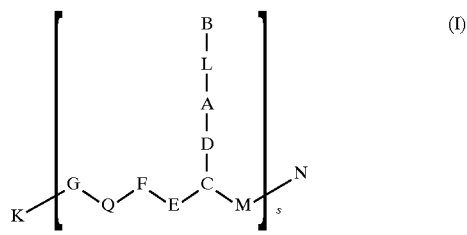

and to the corresponding monomers, whose radicals have the meaning given in the description, and to their use as medicaments or diagnostic aids.

12 Claims, No Drawings

NUCLEIC ACID-BINDING OLIGOMERS POSSESSING C-BRANCHING FOR THERAPY AND DIAGNOSTICS

This application is a divisional of U.S. Ser. No. 08/300,910 filed Sep. 6, 1994.

The specific switching-off of gene expression by complementary nucleic acids, so-called antisense oligonucleotides, represents a new therapeutic approach. Possible applications extend from the treatment of viral infections through to the therapy of cancer (S. Agrawal, Tibtech 10, 152 (1992); W. James, Antiviral Chemistry & Chemotherapie 2, 191 (1991); B. Calabretta, Cancer Research 51, 4505 (1991)). The control of gene expression is effected at the DNA and RNA level and is achieved even with unmodified oligonucleotides (C. Helene, Anti-Cancer Drug Design 6, 569 (1991); E. Uhlmann, A. Peyman, Chemical Reviews 90, 543 (1990)). However, owing to insufficient stability towards enzymes and inadequate uptake into cellular systems, these oligonucleotides are not suitable for therapeutic applications. Therapeutic applications require chemically modified antisense oligonucleotides.

Oligonucleotides possessing modified internucleotide phosphate or a phosphate-free internucleotide linkage have been systematically investigated in many studies; however, their synthesis has proved to be very elaborate and observed therapeutic effects have proved to be unsatisfactory (E. Uhlmann, A. Peyman, Chemical Reviews 90, 543 (1990)).

One alternative to modifying or substituting the phosphate group in nucleic acids is completely to replace ribose and phosphate by another backbone. This concept was realized for the first time by Pitha et al., who replaced ribose phosphate by poly-N-vinyl derivatives, leading to so-called "plastic DNA" (J. Pitha, P.O.P. Ts'O, J. Org. Chem. 33 1341 (1968); J. Pitha, Adv. Polym. Sci. 50, 1, (1983)). However, this does not permit the specific construction of defined sequences.

The synthesis of defined sequences is achieved if, for example, a polyamide backbone, which is built up stepwise in analogy with conventional peptide synthesis (M. Bodanszky, Principles of Peptide Synthesis, Springer, Berlin, 1984), is used in place of sugar phosphate. This concept has been realized by a variety of research groups (B. V. Tyaglov, V. I. Permogorov, N. A. Chernykh, Yu. A. Semiletov, K. Konde, Yu. P. Shvachkin, Zh. Obshch. Khim. 57, 1393 (1987); J. E. Summerton et al. WO 86/05518; R. S. Varma et al. WO 92/18518; 0. Buchardt et al. WO 92/20702; H. Wang, D. D. Weller, Tetrahedron Letters 32, 7385 (1991); P. Garner, J. U. Yoo, Tetrahedron Letters 34, 1275(1993); S. -B. Huang, J. S. Nelson, D. D. Weller, J. Org. Chem. 56, 6007 (1991); H. De Koning, U. K. Pandit, Rec. Trav. Chim. 91 1069 (1971); A. B. Cheikh, L. E. Orgel, J. Mol. Evol., 30, 315 (1990)).

Polyamide nucleic acids are also suitable for diagnostic and molecular-biological applications (Buchardt et al. WO 92/20703).

The authors have synthesized new nucleic acid-binding oligomers possessing a C-branching, and they were found to bind surprisingly well to DNA and RNA. The substances are suitable for controlling gene expression and exhibit antiviral properties. Furthermore, substances of this type can be used in diagnostics and molecular biology for isolating, identifying and quantifying nucleic acids.

The invention relates to compounds of the general formula (I)

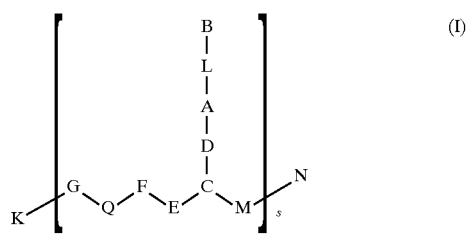

in which

A represents —CO—, —CHR— or —CRR'—,

B independently of one another is selected from a group consisting of: —H, —OH, $(C_1-C_4)$-alkanoyl, DNA intercalators, aromatic radicals, heterocyclic radicals, naturally occurring nucleic bases, such as thymine, uracil, cytosine, adenine, guanine, hypoxanthine, inosine or derivatives obtained from these by chemical modification, and halogenated precursors of these nucleic bases, and protected derivatives of the nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NH—, —NR—, —CHR—, —CR'—, —O— or —S—, A and E can be linked to each other via an alkyl chain [(—CH$_2$)$_n$—where n=0, 1, 2], F represents —CH$_2$—, —CO—, —SO$_2$—, —SO— or —CS—, Q represents (—CR$^1$R$^2$)$_m$—, where m is 0, 1 or 2 and R$^1$ and R$^2$ independently of one another are selected from a group consisting of radicals of natural or unnatural amino acids, such as, for example:

glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-tri-azolylalanine, 2-pyridylalanine, 3-pyridylalanine, 4-pyridylalanine, 1-naphthylalanine or 2-naphthyl-alanine, if appropriate having protective groups, where Q stereochemically uniformly exists in the L form or the D form, G and Q can be linked to each other via an alkyL chain [(—CH$_2$)$_n$—where n=0, 1, 2], G represents —NH—, —NR—, —O— or —S—, M represents —CH$_2$—, —Co—, —SO$_2$—, —SO— or —CS—, L represents (CH$_2$)$_p$, where p=0, 1, 2, —CHR— or —CRR'—, K represents carrier system, reporter ligand, H or solubilizing group, N represents carrier system, reporter ligand, OH or solubilizing group and s represents a value from 1 to 30.

General definition of the radicals R and R':

R and R', independently of one another, can be selected from the following group: H, OH, alkyl (it being possible for alkyl to be methyl, ethyl, n-propyl, isopropyl, n-butyl, isobutyl or tert-butyl), aralkyl (it being possible for aralkyl to be benzyl, α-naphthylmethyl or β-naphthylmethyl) or aryl (it being possible for aryl to be phenyl, 2-pyridyl or 4-pyridyl, if appropriate substituted by methyl, halogen or $NO_2$).

Preferred compounds of the general formula (I) are those in which

A represents —CO—, —CHR— or —CRR'—,

B independently of one another is selected from a group consisting of: —H, —OH, $(C_1-C_4)$-alkanoyl, DNA intercalators, aromatic radicals, heterocyclic radicals, naturally occurring nucleic bases, such as thymine, uracil, cytosine, adenine, guanine, hypoxanthine, inosine and halogenated precursors of these nucleic bases, and protected derivatives of the nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NR—, —NH—, —CHR—, —CRR'— or —O—, A and E can be linked to each other via an alkyl chain $[(-CH_2)_n$—where n=0, 1, 2], F represents —CH$_2$—, —CO—, —SO$_2$—, —SO— or —CS—, Q represents $(—CR^1R^2)_m$—, where m is 0, 1 or 2 and $R^1$ and $R^2$ independently of one another are selected from a group consisting of radicals of natural or unnatural amino acids, such as, for example: glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, 4-nitrophenylalanine, 3-nitrophenylalanine, 2-nitrophenylalanine, 1-naphthylalanine or 2-naphthylalanine, if appropriate having protective groups, where Q stereochemically uniformly exists in the L form or the D form, G and Q can be linked to each other via an alkyl chain $[(-CH_2)_n$—where n=0, 1, 2], G represents —NH—, —NR— or —O—, M represents —CH$_2$—, —CO—, —SO$_2$— or —CS—, L represents $(CH_2)_p$ where p=0, 1, 2, —CHR— or —CRR'—, K represents carrier system, reporter ligand, H or solubilizing group, N represents carrier system, reporter ligand, OH or solubilizing group and s represents a value from 1 to 30.

General definition of the radicals R and R':

R and R', independently of one another, can be selected from the following group: H, OH, alkyl (it being possible for alkyl to be methyl, ethyl, n-propyl or n-butyl), benzyl or aryl (it being possible for aryl to be phenyl, if appropriate substituted by methyl, halogen or $NO_2$).

Particularly preferred compounds of the general formula (I) are those in which

A represents —CO—, —CHR— or —CRR'—,

B independently of one another is selected from a group consisting of: —H, —OH, $(C_1-C_4)$-alkanoyl, DNA intercalators, aromatic radicals, hetero-cyclic radicals, naturally occurring nucleic bases, such as thymine, uracil, cytosine, adenine, guanine, hypoxanthine, inosine and halogenated precursors of these nucleic bases, and protected derivatives of the nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NR—, —NH— or —CHR—, A and E can be linked to each other via an alkyl chain $[(-CH_2)_n$—where n=0, 1, 2], F represents —CH$_2$—, —CO— or —CS—, Q represents $(—CR^1R^2)_m$—, where m is 0, 1 or 2 and $R^1$ and $R^2$ independently of one another are selected from a group consisting of radicals of natural or unnatural amino acids, such as, for example: glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, if appropriate having protective groups, where L stereochemically uniformly exists in the L form or the D form, G and Q can be linked to each other via an alkyl chain $[(-CH_2)_n$—where n=0, 1, 2], G represents —NH—, —NR— or —O—, M represents —CH$_2$—, —CO— or —CS—, L represents $(CH_2)_p$ where p=0, 1, 2, —CHR— or —CRR'—, K represents carrier system, reporter ligand, H or solubilizing group, N represents carrier system, reporter ligand, OH or solubilizing group and s represents a value from 1 to 30.

General definition of the radicals R and R':

R and R', independently of one another, can be selected from the following group: H, OH, methyl or benzyl.

Monomer and dipeptide units for peptide nucleic acids

The invention furthermore relates to compounds of the general formula (II)

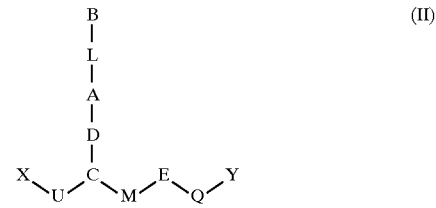

in which

A represents —CO—, —CHR— or —CRR'—,

B independently of one another is selected from a group consisting of: —H, —OH, $(C_1-C_4)$-alkanoyl, DNA intercalators, aromatic radicals, hetero-cyclic radicals, naturally occurring nucleic bases, such as thymine, uracil, cytosine, adenine, guanine, hypoxanthine, inosine or derivatives obtained from these by chemical modification, and halogenated precursors of these nucleic bases, and protected derivatives of these nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NH—, —NR—, CHR—, —CRR'—, —O— or —S—, Q represents (—CR$^1$R$^2$)$_m$—, where m is 0, 1 or 2 and R$^1$ and R$^2$ independently of one another are selected from a group consisting of radicals of natural or unnatural amino acids, such as, for example:

glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-triazolylalanine, 2-pyridylalanine, 3-pyridylalanine, 4-pyridylalanine, 1-naphthylalanine or 2-naphthyl-alanine, if appropriate having protective groups, where Q stereochemically uniformly exists in the L form or the D form, E and Q can be linked to each other via an alkyl chain [(—CH$_2$)$_n$—where n=0, 1, 2], M represents —CH$_2$—, —CO—, —SO$_2$—, —SO— or —CS—, L represents (CH$_2$)$_p$ where p=0, 1, 2, —CHR— or —CRR'—, U represents —NH— or —NR—, X represents any protective group known from peptide chemistry, H or any natural or unnatural amino acid in protected or unprotected form and Y represents COOH, CSOH, CH$_2$OH or COOR" where R" is any protective group from peptide chemistry, carrier, reporter ligand or solubilizing group.

General definition of the radicals R and R':

R and R', independently of one another, can be selected from the following group: H, OH, alkyl (it being possible for alkyl to be methyl, ethyl, n-propyl, isopropyl, n-butyl, isobutyl or tert-butyl), aralkyl (it being possible for aralkyl to be benzyl, α-naphthylmethyl or β-naphthylmethyl) or aryl (it being possible for aryl to be phenyl, 2-pyridyl or 4-pyridyl, if appropriate substituted by methyl, halogen or NO$_2$).

Preferred compounds of the general formula (II) are those in which

A represents —CO—, —CHR— or —CRR'—,

B independently of one another is selected from a group consisting of: —H, —OH, (C$_1$–C$_4$)-alkanoyl, DNA intercalators, aromatic radicals, heterocyclic radicals, naturally occurring nucleic bases, such as thymine, uracil, cytosine, adenine, guanine, hypoxanthine, inosine and halogenated precursors of these nucleic bases, and protected derivatives of these nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NR—, —NH—, —CHR—, —CRR'— or —O—, Q represents (—CR$^1$R$^2$)$_m$—, where m is 0, 1 or 2 and R$^1$ and R$^2$ independently of one another are selected from a group consisting of radicals of natural or unnatural amino acids, such as, for example: glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, 4-nitrophenylalanine, 3-nitrophenylalanine, 2-nitrophenylalanine, 1-naphthylalanine or 2-naphthylalanine, if appropriate having protective groups, where Q stereochemically uniformly exists in the L form or the D form, E and Q can be linked to each other via an alkyl chain [(—CH$_2$)$_n$—where n=0, 1, 2], M represents —CH$_2$—, —CO—, —SO$_2$—, —SO— or —CS—, L represents (CH$_2$)$_p$ where p=0, 1, 2, —CHR— or —CRR'—, U represents —NH— or —NR—, X represents any protective group known from peptide chemistry, H or any natural or unnatural amino acid in protected or unprotected form and Y represents COOH, CSOH, CH$_2$OH or COOR" where R" is any protective group from peptide chemistry, carrier, reporter ligand or solubilizing group.

General definition of the radicals R and R':

R and R', independently of one another, can be selected from the following group: H, OH, alkyl (it being possible for alkyl to be methyl, ethyl, n-propyl or n-butyl), benzyl or aryl (it being possible for aryl to be phenyl, if appropriate substituted by methyl, halogen or NO$_2$).

Particularly preferred compounds of the general formula (II) are those in which

A represents —CO—, —CHR— or —CRR'—,

B independently of one another is selected from a group consisting of: —H, —OH, (C$_1$–C$_4$)-alkanoyl, DNA intercalators, aromatic radicals, hetero-cyclic radicals, naturally occurring nucleic bases, such as thymine, uracil, cytosine, adenine, guanine, hypoxanthine, inosine and halogenated precursors of these nucleic bases, and protected derivatives of these nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NR—, —NH—, —CHR— or —O—, Q represents (—CR$^1$R$^2$)$_m$—, where m is 0, 1 or 2 and R$^1$ and R$^2$ independently of one another are selected from a group consisting of radicals of natural or unnatural amino acids, such as, for example: glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, if appropriate having protective groups, where L stereochemically uniformly exists in the L form or the D form, E and Q can be linked to each other via an alkyl chain [(-CH$_2$)$_n$—where n=0, 1, 2], M represents —CH$_2$—, —CO— or —CS—, L represents (CH$_2$)$_p$ where p=0, 1, 2, —CHR— or —CRR'—, U represents —NH— or —NR—, X represents any protective group known from peptide chemistry, H or any natural or unnatural amino acid in protected or unprotected form and Y represents COOH, CSOH, CH$_2$OH or COOR" where R" is any protective group from peptide chemistry, carrier, reporter ligand or solubilizing group.

General definition of the radicals R and R':

R and R', independently of one another, can be selected from the following group: H, OH, methyl or benzyl.

The invention also relates to compounds of the general formula (III)

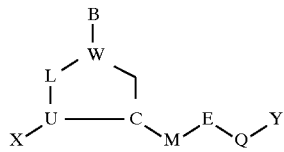

(III)

in which

A represents —CO—, —CHR— or —CRR'—,

B independently of one another is selected from a group consisting of: —H, —OH, (C$_1$–C$_4$)-alkanoyl, DNA intercalators, aromatic radicals, hetero-cyclic radicals, naturally occurring nucleic bases, such as thymine, uracil, cytosine, adenine, guanine, hypoxanthine, inosine or derivatives obtained from these by chemical modification and halogenated precursors of these nucleic bases, and protected derivatives of these nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NR—, —CHR—, —CRR'—, —O— or —S—, Q represents (—CR$^1$R$^2$)$_m$—, where m is 0, 1 or 2 and R$^1$ and R$^2$ independently of one another are selected from a group consisting of radicals of natural or unnatural amino acids, such as, for example: glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, 4-nitrophenylalanine, 3-nitrophenylalanine, 2-nitrophenylalanine, 2-, 3- or 4-aminophenylalanine, 3,4-dichlorophenylalanine, 4-iodophenylalanine, 4-methoxyphenylalanine, 1-triazolylalanine, 2-pyridylalanine, 3-pyridylalanine, 4-pyridylalanine, 1-naphthylalanine or 2-naphthylalanine, if appropriate having protective groups, where Q stereochemically uniformly exists in the L form or the D form, E and Q can be linked to each other via an alkyl chain [(—CH$_2$)$_n$—where n=0, 1, 2], M represents —CH$_2$—, —CO—, —SO$_2$—, —SO— or —CS—, U represents —NH— or —NR—, X represents any protective group known from peptide chemistry, H or any natural or unnatural amino acid in protected or unprotected form, Y represents COOH, CSOH, CH$_2$OH or COOR" where R" is any protective group from peptide chemistry, carrier, reporter ligand or solubilizing group and W represents a chiral C atom which can uniformly exist in the S or R configuration.

General definition of the radicals R and R':

R and R', independently of one another, can be selected from the following group: H, OH, alkyl (it being possible for alkyl to be methyl, ethyl, n-propyl, isopropyl, n-butyl, isobutyl or tert-butyl), aralkyl (it being possible for aralkyl to be benzyl, α-naphthylmethyl or β-naphthylmethyl) or aryl (it being possible for aryl to be phenyl, 2-pyridyl or 4-pyridyl, if appropriate substituted by methyl, halogen or NO$_2$)

Preferred compounds of the general formula (III) are those in which

A represents —CO—, —CHR— or —CRR'—,

B independently of one another is selected from a group consisting of: —H, —OH, (C$_1$–C$_4$)-alkanoyl, DNA intercalators, aromatic radicals, heterocyclic radicals, naturally occurring nucleic bases, such as thymine, uracil, cytosine, adenine, guanine, hypoxanthine, inosine and halogenated precursors of these nucleic bases, and protected derivatives of these nucleic bases having the protective groups which are customary in nucleotide or peptide chemistry, C represents —CH— or —CR—, where C can uniformly exist in the S or R configuration, D represents —NH—, —CH$_2$—, —CHR— or —CRR'—, E represents —NR—, —NH—, —CHR—, —CRR'— or —O—, Q represents (—CR$^1$R$^2$)$_m$—where m is 0, 1 or 2 and R$_1$ and R$^2$ independently of one another are selected from a group consisting of radicals of natural or unnatural amino acids, such as, for example: glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, 4-nitrophenylalanine, 3-nitrophenylalanine, 2-nitrophenylalanine, 1-naphthylalanine or 2-naphthylalanine, if appropriate having protective groups, where Q stereochemically uniformly exists in the L form or the D form, E and Q can be linked to each other via an alkyl chain [(—CH$_2$)$_n$—where n=0, 1, 2], M represents —CH$_2$—, —CO—, —SO$_2$—, —SO— or —CS—, U represents —NH— or —NR—, X represents any protective group known from peptide chemistry, H or any natural or unnatural amino acid in protected or unprotected form, Y represents COOH, CSOH, CH$_2$OH or COOR" where R" is any protective group from peptide chemistry, carrier, reporter ligand or solubilizing group and W represents a chiral C atom which can uniformly exist in the S or R configuration.

General definition of the radicals R and R':

R and R', independently of one another, can be selected from the following group: H, OH, alkyl (it being possible for alkyl to be methyl, ethyl, n-propyl or n-butyl), benzyl or aryl (it being possible for aryl to be phenyl, if appropriate substituted by methyl, halogen or $NO_2$).

Particularly preferred compounds of the general formula (III) are those in which A represents —CO—, —CHR— or —CRR'—, B independently of one another is selected from a group consisting of: —H, —OH, $(C_1$–$C_4)$-alkanoyl, DNA intercalators, aromatic radicals, hetero-cyclic radicals, naturally occurring nucleic bases, such as thymine, uracil, cytosine, adenine, guanine, hypoxanthine, inosine and halogenated precursors of these nucleic bases, and protected derivatives of these nucleic bases having the protective groups which are customary in nucleotide or peptide chemistry, C represents —CH— or —CR—, where C can uniformly exist in the S or R configuration, D represents —NH—, —$CH_2$—, —CHR— or —CRR'—, E represents —NR—, —NH—, —CHR— or —O—, Q represents $(-CR^1R^2)_m$—, where m is 0, 1 or 2 and $R^1$ and $R^2$ independently of one another are selected from a group consisting of radicals of natural or unnatural amino acids, such as, for example:

glycine, alanine, valine, leucine, isoleucine, serine, threonine, cysteine, methionine, phenylalanine, tyrosine, histidine, tryptophan, lysine, ornithine, aspartic acid, glutamic acid, asparagine, glutamine, arginine, proline, hydroxyproline, sarcosine, aminoisobutyric acid, dehydroamino acids, such as, for example, dehydroalanine, dehydro-α-aminobutyric acid, other unnatural amino acids, such as phenylglycine, if appropriate having protective groups, where L stereochemically uniformly exists in the L form or the D form, E and Q can be linked to each other via an alkyl chain [(—$CH_2)_n$—where n=0, 1, 2], M represents —$CH_2$—, —CO— or —CS—, U represents —NH— or —NR—, X represents any protective group known from peptide chemistry, H or any natural or unnatural amino acid in protected or unprotected form, Y represents COOH, CSOH, $CH_2OH$ or COOR" where R" is any protective group from peptide chemistry, carrier, reporter ligand or solubilizing group and W represents a chiral C atom which can uniformly exist in the S or R configuration.

General definition of the radicals R and R':
R and R', independently of one another, can be selected from the following group: H, OH, methyl or benzyl.

Carrier system or reporter ligand is to be understood as meaning a cell-specific binding and recognition agent which binds specifically to the cell surface and brings about internalization of the nucleic acid-binding oligomers on which the invention is based. Internalization can be effected in various ways, for example by endocytosis or by active transport mechanisms.

The structure of the cell surface can be a protein, polypeptide, carbohydrate, lipid or a combination of these. Typically, uptake into the cell is brought about by surface receptors. This is why the binding and recognition agent can be a natural or synthetic ligand of a receptor.

The ligand can be a protein, polypeptide, carbohydrate, lipid or a combination of these which is provided with functional groups which are arranged in such a manner that they can be recognized by the cell-surface structure. It can also be a component or the entirety of a biological organism, for example of a virus or a cell, or artificial transport systems, such as, for example, liposomes. It can furthermore be an antibody or an analogue of an antibody.

Different ligands must be employed for directing the oligomers to different cells.

Ligands which are suitable for directing the oligomers to macrophages are, preferably, carbohydrates, such as, for example, mannose, polycations, such as, for example, polylysines, polyarginines, polyornithines, basic proteins, such as, for example avidin, and also glycopeptides, peptides or lipopeptides (G. Y. Chu et al., WO 9304701).

Solubilizing groups are to be understood as meaning functional groups which solubilize the oligomers in water. These can be, for example, esters or amides of amino acids, hydroxycarboxylic acids, aminosulphonic acids, hydroxysulphonic acids or diamines. Preferred substances are amides of diaminocarboxylic acid, such as ornithine, lysine or 2,4-diaminobutyric acid.

Peptide-nucleic acids possessing an α, ω-diaminocarboxylic acid backbone

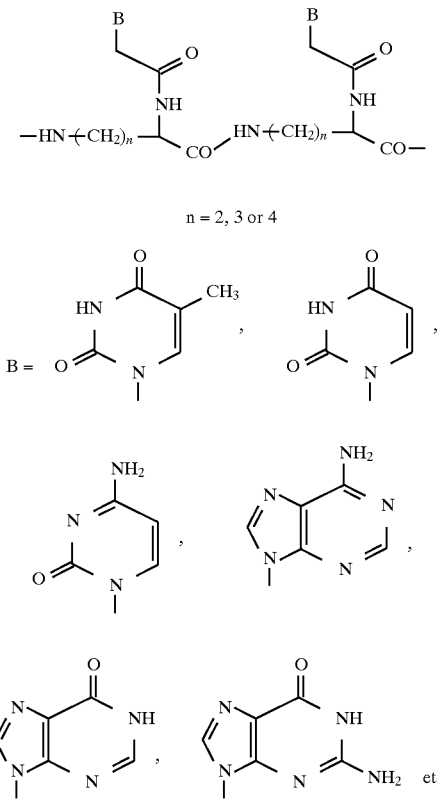

In the case of compounds of this type, the sugar phosphate backbone of the natural nucleic acids is replaced by a polymer of α, ω-diaminocarboxylic acids, such as, for example, lysine, ornithine or 2,4-diaminobutyric acid, which polymer is linked via the side chains. The nucleic bases are bonded to the a-amino groups via acyl spacers. The results are relatively flexible oligomers.

Peptide-nucleic acids possessing a 2-aminobutyrylglycine backbone

In the case of compounds of this type, the ribose phosphate, or deoxyribose phosphate, backbone of RNA or DNA is replaced by a peptide backbone of 2-aminobutyryl-glycine dipeptides. The resulting oligomer is distinguished by its high flexibility. Moreover, the chain construction of chiral α-amino acids greatly increases the range of variation (modification of chirality, use of other spacers in place of glycine) in the synthesis of oligomers.

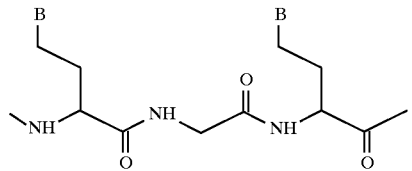

(B is defined as above)

Peptide-nucleic acids possessing a pyrrolidine-2-carboxyglycine backbone

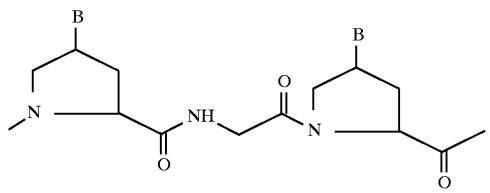

(B is defined as above)

In this type of structure, the sugar phosphate backbone of the natural nucleic acids is replaced by a peptide backbone of pyrrolidine-2-carboxyglycine dipeptides. The use of pyrrolidine-2-carboxylic acid in the backbone results in rigid structures. Variation of the centres of chirality on the pyrrolidine-2-carboxylic acid gives oligomers of different conformation. Moreover, this approach also allows the glycine spacer to be replaced by other spacers, such as, for example, other amino acids or hydroxycarboxylic acids.

Biological properties and effects of these compounds
Stability to proteases and nucleases In addition to their chain length, their sequence and their cell permeability, resistance to proteases and nucleates plays an important role for the biological effect of nucleic acid-binding oligomers.

The oligomers synthesized were therefore compared with natural oligonucleotide diesters with regard to their stability to proteases and nucleases.

For this purpose, the nucleic acid-binding oligomers were treated with non-specific and specific proteases, such as, for example, pronase E, proteinase K, trypsin, endoprotease, Lys-C, V8 protease, protease IX, protease XXI, and nucleases, such as, for example, S1 nuclease, Ba131 nuclease, phosphodiesterase, and cell extracts, organ extracts, blood serum and blood extracts which contain various nucleases and proteases. The oligomers were examined for degradation by polyacrylamide gel electrophoresis and UV shadowing on TLC plates containing UV indicator and by silver-staining of the polyacrylamide gels.

Natural oligonucleotide diesters only have a low degree of stability to nucleases. They are completely degraded within 30 minutes to 1 hour.

By contrast, nucleic acid-binding oligomers possessing C-branching are fully resistant to nucleases and proteases and are therefore particularly well suited for use as antisense inhibitors.

Binding to DNA single strands as determined by gel shift analyses

The nucleic acid-binding oligomers described herein were examined in gel shift analyses. In these band shift experiments, the altered migratory behaviour of radio-labelled oligonucleotides was measured by polyacrylamide gel electrophoresis following hybridization to the oligomers described herein. Owing to the formation of the hybrids, the hybridized oligonucleotides migrate more slowly in the electrophoresis, firstly because the molecular weight is increased and secondly because the charge per unit of mass in the hybrid complex is diminished. As compared to a non-hybridized oligonucleotide, their migratory behaviour in the gel is retarded (gel retardation).

Strand displacement in double-stranded plasmid DNA

Nucleic acid-binding oligomers are biologically active in that they exhibit sequence-selective binding to double-stranded DNA (dsDNA) by strand displacement. This effect of nucleic acid-binding oligomers can be demonstrated in in-vitro tests as being sequence- and concentration-dependent.

Inhibition of gene expression (in vitro translation test)

Nucleic acid-binding oligomers which have proved to be of interest in gel shift and strand displacement experiments were tested for their ability to inhibit the protein synthesis of the specific genes. A prerequisite for this is that the corresponding sequence of the nucleic acid-binding oligomer is contained in the relevant gene in parallel or antiparallel base sequence. It emerged in the in-vitro translations that the nucleic acid-binding oligomers described herein are very potent sequence-specific inhibitors of gene expression. In this case, shorter sequences and lower concentrations than in the case of oligonucleotides with identical sequences were sufficient for better inhibition.

The target sequence can be derived from the promoter of a disease-triggering gene. Target sequences which bind enhancer or transcription factors and DNA polymerase or RNA polymerase from genes of viruses, bacteria, fungi, endoparasites, oncogens or genes which are involved in the expression of inflammatory diseases, autoimmune disorders, or cardiovascular disorders, such as high blood pressure or arteriosclerosis, may, in particular, be mentioned here as potential target sequences for the therapeutical application of nucleic acid-binding oligomers.

In addition to oligomers which possess C-branching, the relevant pharmaceutical preparations contain the auxiliaries which are conventional for parenteral preparations, such as, for example, buffers and/or stabilizers or liposome formulations. Topical application is also conceivable. The preparations which can be employed for this purpose are, for example, ointments, creams, solutions or plasters which, in addition to the active substance, contain pharmaceutical auxiliaries which are suitable for this type of application.

Therapeutically active nucleic acid-binding oligomers as they are described herein can not only inhibit gene expression by sequence-selective binding to mRNA, as mentioned above, but, of course, they can also inactivate the promoter and enhancer sequences of genes to be inhibited, in a sequence-selective manner, due to their characteristic of displacing double-stranded DNA.

For this type of application for gene inactivation, nucleic acid-binding oligomers contain not only nucleic base sequences of (−)-strand DNA, but also the (+)-strand DNA sequence of the target DNA to be inhibited.

Synthesis of monomeric units

Monomers for peptide-nucleic acids possessing an α, ω-diaminocarboxylic acid backbone

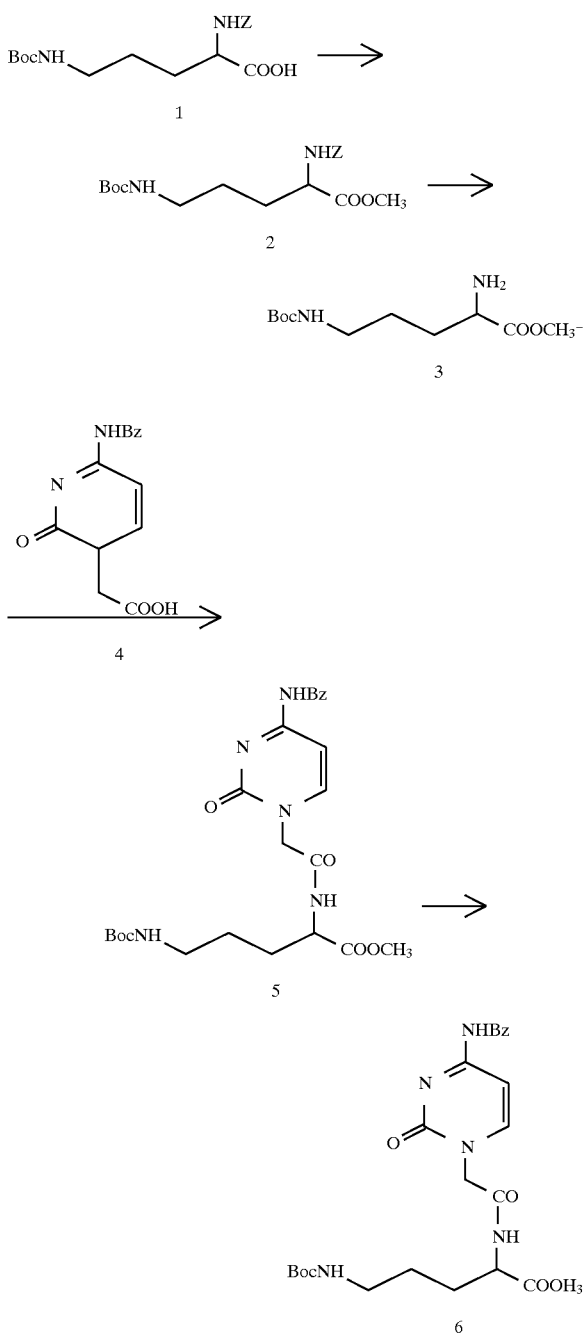

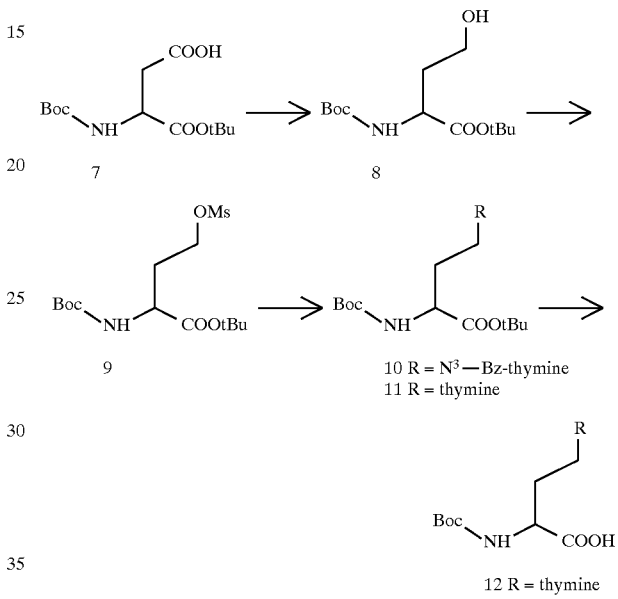

The synthesis of the monomers for peptide-nucleic acids possessing an α, ω-diaminocarboxylic acid backbone will be illustrated using the cytosine-ornithine derivative 6 by way of example.

α-N-(Benzyloxycarbonyl) -δ-N-(tert-butoxycarbonyl)-L-ornithine 1 is converted into the methyl ester 2 using methyl iodide and caesium carbonate. The α-N-(benzyloxycarbonyl) protective group is removed hydrogenolytically. The derivative 3, which has a free α-amino group, is reacted with $N^4$-benzoyl-1-carboxymethyl-cytosine 4 in the presence of a condensing agent, for example N,N'-dicyclohexylcarbodiimide. This gives rise to 5. Alternatively, the linkage can also be carried out using activated esters, for example pentafluorophenyl esters of the 1-carboxymethyl nucleic bases.

The methyl ester in 5 is hydrolysed in the presence of a base. The benzoate protective group is not affected.

The peptide nucleic acid 6 is suitable for-use in solid-phase peptide synthesis under "Boc conditions".

Derivatives of other nucleic bases and other α, ω-diamino-carboxylic acids, such as, for example, lysine and 2,4-diaminobutyric acid, are accessible by way of analogy. Moreover, the D-amino acid derivatives can also be used instead of the L-amino acid derivatives.

Monomers for peptide-nucleic acids possessing a 2-aminobutyrylglycine backbone

The thymine unit is given as an example for the synthesis of monomers:

N-tert-Butyloxycarbonyl-L-aspartate is reduced with a complex hydride in an aprotic bipolar solvent to give N-tert-butyloxycarbonyl-L-homoserine tert-butyl ester 8 (apart from L-aspartic acid, D-aspartic acid can also be used for the synthesis). The hydroxyl group is converted into a leaving group (for example into 9) and substituted for a heterocyclic nucleic base (for example 10). The protective groups are subsequently eliminated and the α-amino function is protected (for example 12). The 2-aminobutyrylglycine backbone is obtained in the oligomerization process by the alternating use of the 2-aminobutyryl unit and a glycine unit.

Other types of backbone are obtained quite simply by using other spacers during the oligomerization process in place of glycine.

Monomers for peptide-nucleic acids possessing a pyrrolidine-2-carboxyl-glycine backbone The thymine unit is given as an example for the synthesis of monomers:

A hydroxyproline unit which is protected N- and C-terminally (for example 13 or 14) is reacted with a nucleic base in a Mitsunobu reaction in an aprotic solvent, giving rise to, for example, 15 or 16. The ester is subsequently cleaved and, in the case of 15 or 16, the nucleic base is also deprotected, giving rise to 17. Starting from the L-trans-hydroxyproline derivative 14, this gives the L-cis-pyrrolidine-2-carboxylic acid product 17. To reach the series of the L-trans-pyrrolidine-2-carboxylic acid products, L-cis-hydroxy-proline derivatives are required, and these are obtained from the L-trans-hydroxyproline derivatives by chirality reversal in the 4-position (for example using the route from 14 in a Mitsunobu reaction to 19, via 18). The further synthetic route to give 21 is then effected analogously to the reactions of 14 to give 17. Apart from the L-cis and L-trans products, the D-cis and D-trans products may also be prepared.

Other types of backbone are obtained by using other spacers in the oligomerization process in place of glycine.

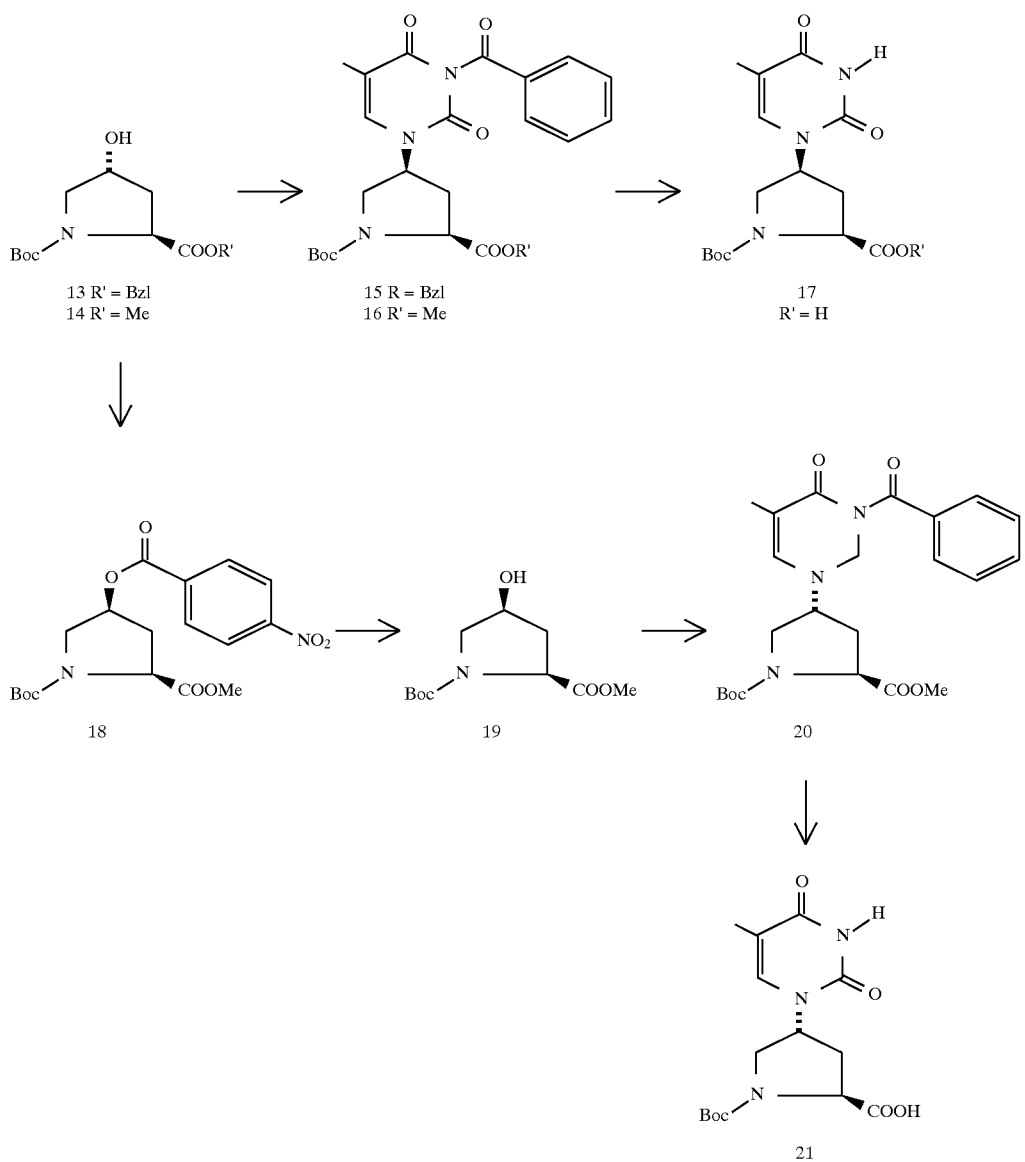

Dipeptide units for peptide-nucleic acids possessing a 2-aminobutyryl-glycine backbone To synthesize the dipeptides, for example, N-Boc-4-(thymin-1-yl)-2-L-aminobutyric acid 12 is coupled with glycine methyl ester in the presence of EDCI*HCl and HOBt*H₂O to give 22. The ester is subsequently hydrolysed, giving rise to compound 23.

Apart from glycine, other natural or unnatural amino acids may also be subjected to a coupling reaction in a similar manner. The dipeptides obtained are then used for oligomerization.

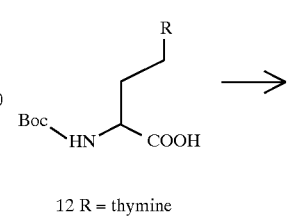

12 R = thymine

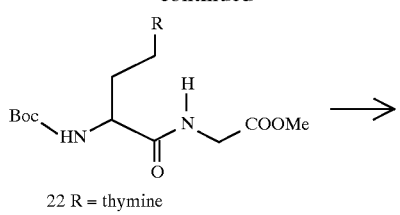

22 R = thymine

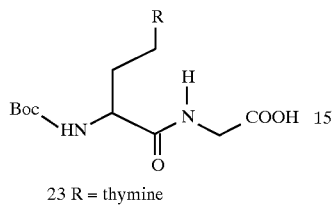

23 R = thymine

Dipeptide units for peptide-nucleic acids possessing a pyrrolidine-2-carboxyl-glycine backbone To synthesize the dipeptides, for example, 2S,4S-N-Boc-4-(thymin-1-yl)pyrrolidine-2-carboxylic acid 17 is coupled with glycine methyl ester in the presence of EDCI*HCl and HOBt*H₂O to give 24. The ester is subsequently hydrolysed, which gives rise to compound 25.

Apart from glycine, other natural or unnatural amino acids may also be subjected to a coupling reaction in a similar manner. The dipeptides obtained are then used for oligomerization.

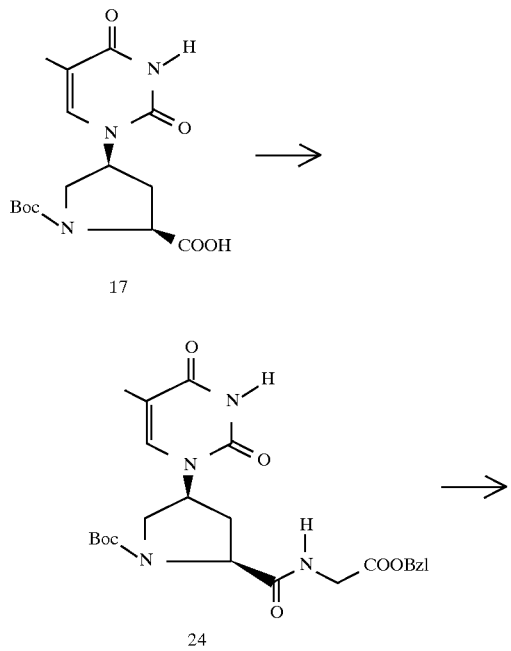

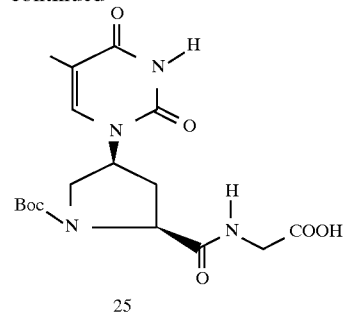

25

Oligomer syntheses

The linking of the units to form oligomers is effected by solid-phase peptide synthesis. PAM, MBHA or HMP resins, manufactured by Applied Biosystems, were used as polymeric supports. The units are linked either by the Fmoc or Boc process in analogy with conventional peptide synthesis. Activation of the units is effected in N-methyl-2-pyrrolidone by reaction with hydroxybenzotriazole/dicyclohexylcarbodiimide or pentafluorophenol/dicyclohexylcarbodiimide. The sequences are subsequently cleaved off by being treated with HF or trifluoromethanesulphonic acid (Boc method, PAM or MBHA resin) or by trifluoroacetic acid (Fmoc method, HMP resin). The reaction products are isolated by preparative HPLC on RP 8 using an ascending gradient of trifluoroacetic acid in acetonitrile/water. Sequences having chain lengths of up to 15 units were synthesized by this method. The α, ω-diaminocarboxylic acid units listed below were preferred for the oligomerization. As an alternative to the Boc protective group, the Fmoc protective group may also be employed.

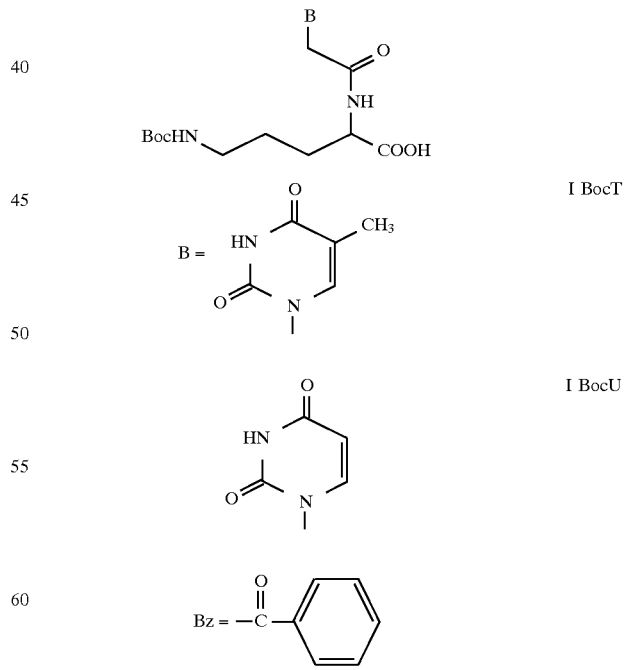

-continued
I BocC^Bz 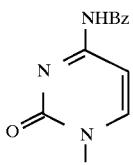
Z = 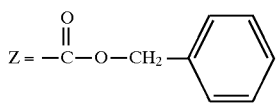
I BocC^Z 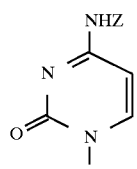
IBocIn 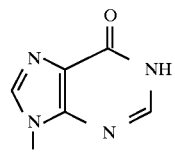
BocA^Bz 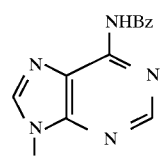
IBocA^z 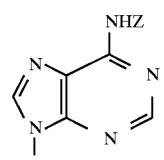
IBocG^z 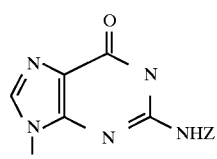
X = 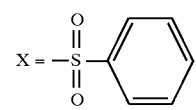
IBocG^x 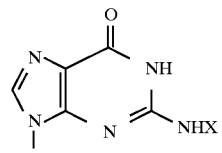
This gives rise to the following synthesis equivalents:
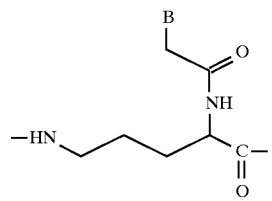
B = 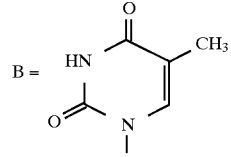  IT
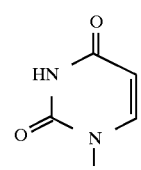  IU
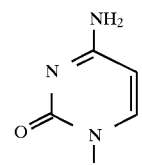  IC
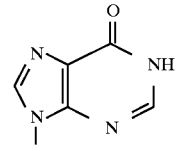  IIn
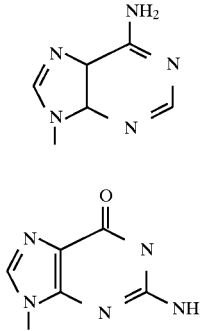
IA
IG
The 2-aminobutyryl units listed below were preferred for the oligomerization. As an alternative to the Boc protective group, the Fmoc protective group may also be employed:
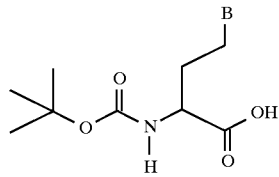

B = 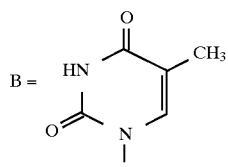 II BocT
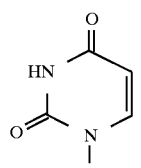 II BocU
Bz = 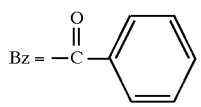
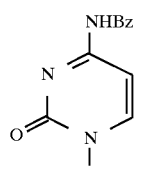 II BocC$^{Bz}$
Z = 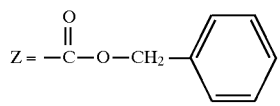
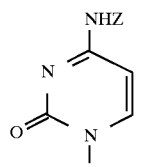 II BocC$^Z$
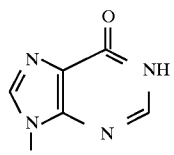 II BocIn
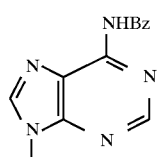 II BocA$^{Bz}$
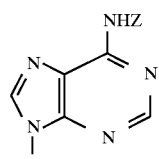 IIBocA$^z$
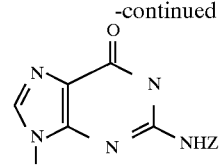 IIBocG$^z$
X = 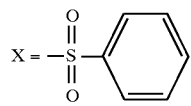
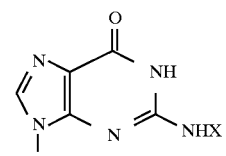 IIBocG$^x$
This gives rise to the following synthesis equivalents:
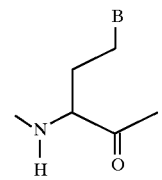
B = 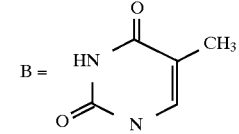 IIT
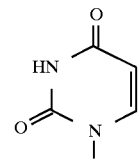 IIU
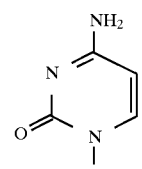 IIC
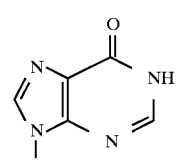 IIIn
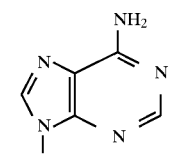 IIA -continued

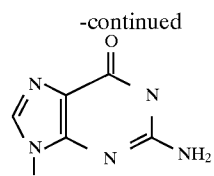 IIG

The pyrrolidone-2-carboxyl units listed below were preferred for the oligomerization. As an alternative to the Boc protective group, the Fmoc protective group may also be employed:

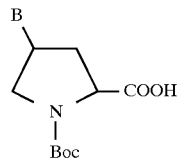

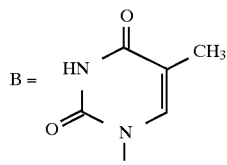 III BocT

B =

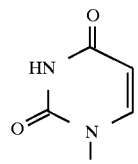 III BocU

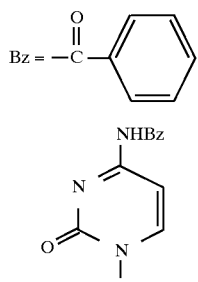

Bz =

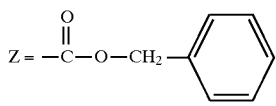 III BocC^Bz

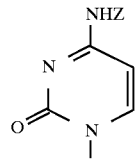

Z =

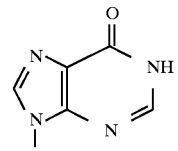 III BocC^Z

III BocIn

-continued

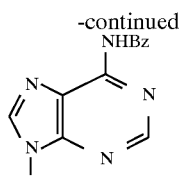 III BocA^Bz

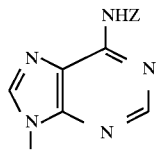 III BocA^z

III BocG^z

X =

III BocG^x

This gives rise to the following synthesis equivalents:

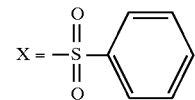

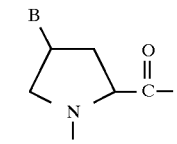 IIIT

B =

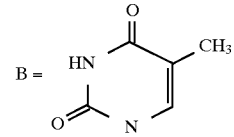 IIIU

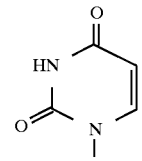

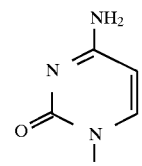 IIIC

-continued

IIIIn

IIIA

IIIG

The dimeric units listed below were also used for the oligomerization. As an alternative to the Boc protective group, the Fmoc protective group may also be employed:

IV BocT

IV BocU

Bz = benzoyl group

IV BocC$^{Bz}$

Z = benzyloxycarbonyl group

-continued

IV BocC$^Z$

IV BocIn

IV BocA$^{Bz}$

IV BocA$^Z$

IV BocG$^Z$

X = phenylsulfonyl group

IV BocG$^X$

This gives rise to the following synthesis equivalents:

IV T

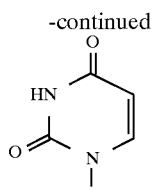
IV U
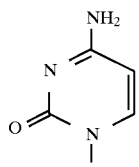
IV C
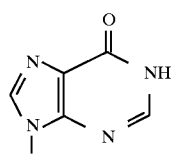
IV In
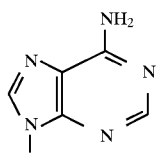
IV A
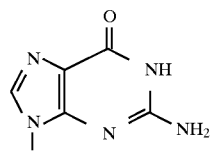
IV G
In the case of the 2-aminobutyryl type, dimeric units were also employed for the oligomerization:
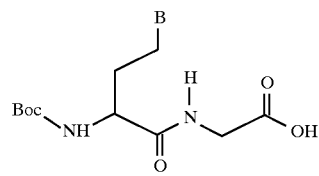
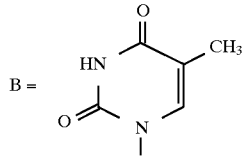
B =
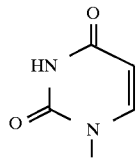
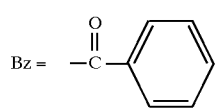
Bz =
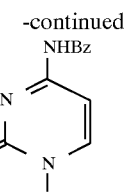
V BocC$^{Bz}$
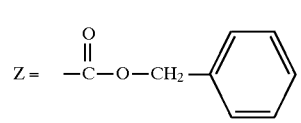
Z =
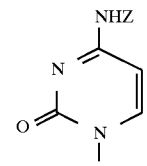
V BocC$^Z$
V BocIn
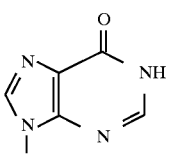
V BocA$^{Bz}$
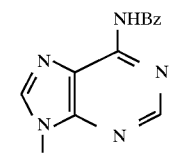
V BocA$^Z$
V BocG$^Z$
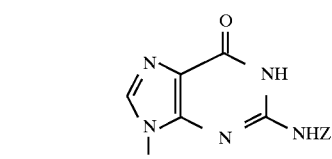
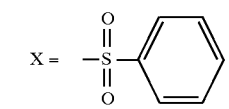
X =
V BocG$^X$
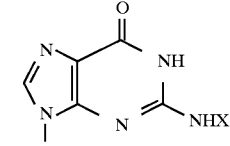
V BocT
V BocU
This gives rise to the following 2-aminobutyrylglycine syntheses equivalents:

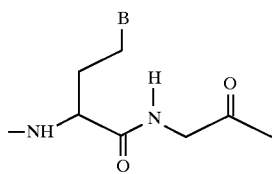

B =

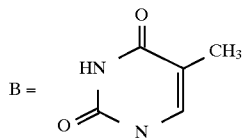 VT

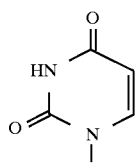 VU

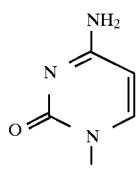 VC

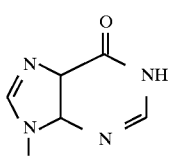 V In

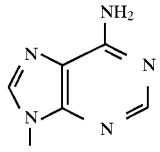 VA

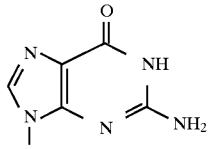 VG

EXAMPLES

Monomers

Example 1

α-N-Benzyloxycarbonyl-δ-N-tert-butyloxycarbonyl-L-ornithine methyl ester (2)

A solution of α-N-benzyloxycarbonyl-δ-N-tert-butyloxycarbonyl-L-ornithine (10.0 g; 27 mmol) in anhydrous methanol (135 ml) is brought to pH 9.0 to 9.5 using caesium carbonate, and stirring is continued for 30 minutes at room temperature. The mixture is subsequently concentrated and dried for 30 minutes under a high vacuum. The residue is taken up in anhydrous N,N-dimethylformamide (135 ml) and treated with iodomethane (4.37 g; 30 mmol). The mixture is left to stand for 30 minutes at room temperature, concentrated in vacuo and distilled repeatedly using toluene. The oil which has formed is taken up in chloroform (270 ml) and extracted by shaking with water. The organic phase is dried and concentrated.

Yield: 10.4 g (quantitative). Rf: 0.70 Eluent: toluene/EtOH 1:3

Example 2

δ-N-tert-Butyloxycarbonyl-L-ornithine methyl ester (3)

The product of Example 1 (12.6 g; 33 mmol) is hydrogenated for 46 hours in methanol (330 ml) over palladium on barium sulphate (5%, 9.96 g) at room temperature and ambient pressure. The catalyst (Celite) is subsequently removed by filtration with suction and the filtrate is concentrated.

Yield: 12.6 g (quantitative). Rf: 0.58 Eluent: toluene/EtOH 4:1

Example 3

δ-N-tert-Butyloxycarbonyl-α-N-(thymin-1-yl)acetyl-L-ornithine

A solution of pentafluorophenol (4.22 g; 23 mmol) in anhydrous N,N-dimethylformamide (20 ml) is added to a solution of 1-carboxymethylthymine (4.22 g; 23 mmol) in anhydrous N,N-dimethylformamide (60 ml). N,N'-Dicyclohexylcarbodiimide (4.74 g; 23 mmol), dissolved in anhydrous N,N-dimethylformamide (20 ml), is subsequently slowly added dropwise at 0° C. Stirring of the reaction solution is continued for 3 hours, during which process the solution is allowed to come to room temperature. The solid which has precipitated is filtered off and washed using N,N-dimethylformamide, and δ-N-tert-butyloxy-carbonyl-L-ornithine (4.45 g; 19 mmol), dissolved in N,N-dimethylformamide, is added dropwise to the solution at 0° C. The mixture is stirred for a further 21 hours at room temperature and concentrated in vacuo, this is followed by repeated distillation with toluene, and the product is chromatographed on silica gel using chloroform/methanol (2:1) as the eluent.

Yield: 7.70 g (quantitative) Rf: 0.78 Eluent: CHCl₃/MeOH 1:1

Example 4

N⁴-Benzoyl-1-tert-butyloxycarbonylmethylcytosine tert-Butyl bromoacetate (24 ml; 0.15 mol) is slowly added dropwise at room temperature to a suspension of N⁴-benzoylcytosine (21.5 g; 0.1 mol) and potassium carbonate (13.8 g; 0.1 mol) in anhydrous N,N-dimethylformamide (2.15 l). The heterogeneous mixture is stirred vigorously for 20 hours at room temperature, insoluble educt is subsequently removed by filtration with suction, the filtrate is concentrated in vacuo and repeatedly distilled using toluene, the residue is taken up in chloroform (1.0 l), the mixture is extracted once by shaking with water (0.3 l), and the phases are separated rapidly. The organic phase is refiltered and concentrated.

Yield: 15.23 g (46%) Rf: 0.33 Eluent toluene/EtOH 10:1

Example 5

N₄-Benzoyl-1-carboxymethylcytosine (4)

The product of Example 4 is dissolved in trifluoroacetic acid (170 ml), and the solution is left to stand for 1 hour 45 minutes at room temperature. The product is subsequently subjected five times to co-distillation with toluene, and the product is dried for 24 hours in a desiccator over phosphorus pentoxide/potassium hydroxide.

Yield: 11.8 g (93%). Rf: 0.1 Eluent: toluene/EtOH 1:1

Example 6

α-N-($N_4$-Benzoylcytosin-1-yl)acetyl-δ-N-tert-butyloxy-carbonyl-L-ornithine methyl ester (5)

$N^4$-Benzoyl-1-carboxymethylcytosine (15.76 g; 58 mmol) and δ-tert-butyloxycarbonyl-L-ornithine methyl ester (9.61 g; 39 mmol) are suspended in anhydrous N,N-dimethylformamide (520 ml), and N,N'-dicyclohexylcarbodiimide (11.92 g; 58 mmol) is added. The mixture is stirred for 1 hour at room temperature and then concentrated in vacuo, and the mixture is distilled repeatedly with toluene. The crude product is purified chromatographically on silica gel (eluent: toluene/ethanol 8:1).

Yield: 5.21 g (27%) Rf: 0.47 Eluent: toluene/EtOH 4:1

Example 7

α-N-($N_4$-Benzoylcytosin-1-yl)acetyl-δ-N-tert-butyloxy-carbonyl-L-ornithine (6)

A solution of the product of Example 6 (4.80 g; 8.7 mmol) in dioxane/water (5:1; 70 ml) is treated with lithium hydroxide hydrate (440 mg; 10.5 mmol), and the mixture is allowed to stand for 1.5 hours at room temperature. It is subsequently rendered neutral using 0.5N hydrochloric acid and concentrated. The product crystallizes from methanol.

Yield: 2.09 g (45%)

Example 8

N-Boc-L-homoserine tert-butyl ester (8)

tert-Butyl N-Boc-aspartate (15.4 g; 53.1 mmol) is introduced into absolute THF, and the mixture is cooled to 0° C. At this temperature, 1 equivalent of triethylamine followed by 1 equivalent of ethyl chloroformate are added. The reaction mixture is stirred for 15 minutes at 0° C. and for 5 minutes at room temperature. Precipitated triethylamine hydrochloride is subsequently filtered off with suction, and the filtrate is further reacted directly.

The filtrate is added dropwise to a suspension of $NaBH_4$ in THF, which has previously been cooled to 0° C., and stirring is continued at this temperature for 15 to 20 minutes. The ice-bath is then removed, and stirring of the mixture continues at room temperature for a further 30 to 40 minutes. After the reaction has ended, the mixture is quenched by adding 1N HCl. The phases are subsequently separated, and the organic phase is extracted 3 times in each case by shaking in succession with 100 ml of 1N HCl, saturated $NAHCO_3$ and saturated NaCl solution. The organic phase is separated off, dried over $Na_2SO_4$ and concentrated to dryness on a rotary evaporator. A clear oil remains.

Yield: 12 g (82.2%) Rf: 0.66 Eluent: $CH_2Cl_2$/MeOH 9:1

Example 9

N-Boc-γ-methanesulphonyloxy-L-homoserine tert-butyl ester (9)

N-Boc-L-Homoserine tert-butyl ester (13 g; 47.2 mmol) is dissolved in absolute pyridine, and the solution is cooled to 0° C. 1.1 equivalents of methanesulphonyl chloride are added dropwise at this temperature. The mixture is subsequently stirred for 5 hours at room temperature. After the reaction has ended, the pyridine is distilled off. The residue is covered with a layer of ethyl acetate, and the mixture is extracted 3 times in each case by shaking in succession with 100 ml of 1N HCl, saturated $NaHCO_3$ and saturated NaCl solution. The organic phase is separated off, dried over $Na_2SO_4$ and evaporated to dryness. The residue is taken up in a little ethyl acetate, and the product is precipitated by adding n-hexane.

Yield: 12.9 g (77%) Rf: 0.76 Eluent: ethyl acetate/n-hexane 2:1 M.p.: 93° C.

Example 10a tert-Butyl N-Boc-4-($N^3$-benzoyl-thymin-1-yl)-2-L-amino-butyrate (10)

$N^3$-Benzoyl-thymine (2 equivalents) is introduced into absolute DMF, and 2 equivalents of $K_2CO_3$ are added. The mixture is stirred for 5 minutes at room temperature. The mesylate (9) (1.18 g; 3.36 mmol), dissolved in DMF, is then added dropwise. After the addition has ended, the mixture is heated to 60° C. and stirred for 4 hours at this temperature. After the reaction has ended, the DMF is distilled off, the residue is covered with a layer of ethyl acetate, and this is extracted 3 times in each case by shaking in succession with 20 ml of 1N HCl, saturated $NaHCO_3$ and saturated NaCl solution. The ethyl acetate phase is dried over $Na_2SO_4$ and then evaporated to dryness on a rotary evaporator. The crude product obtained is finally chromatographed on silica gel using ethyl acetate/n-hexane 1:1 as the eluent.

Yield: 897 mg (54.8%) of white foam. Rf: 0.72 Eluent: ethyl acetate/n-hexane 2:1

Example 10b tert-Butyl N-Boc-4-($N^3$-benzoyl-thymin-1-yl)-2-L-amino-butyrate (10)

2.5 equivalents of triphenylphosphine and 2.5 equivalents of DEAD are dissolved in absolute THF and stirred for 5 minutes at room temperature. After this time, the $N^3$-benzoyl-thymine (2 equivalents) is added, and the mixture is stirred for another 5 minutes at room temperature. (8) (3.02 g; 10.98 mmol), which has been dissolved in absolute DMF, is subsequently added dropwise, and stirring is continued overnight at room temperature. After the reaction has ended, the DMF is distilled off, and the crude product is chromatographed on silica gel using ethyl acetate/n-hexane 1:1 as the eluent.

Yield: 3.19 g (58.5%) of white foam. Rf: 0.72 Eluent: ethyl acetate/n-hexane 2:1

Example 11a tert-Butyl N-Boc-4-(thymin-1-yl)-2-L-aminobutyrate (11)

Compound (10) (3.19 g; 5.96 mmol) and $NH_3$ in methanol are stirred overnight at room temperature. The solvent is then distilled off. The crude product obtained is used without further purification for eliminating the Boc and the OtBu protective groups.

Example 11b tert-Butyl N-Boc-4-(thymin-1-yl)-2-L-aminobutyrate (11)

2 equivalents of thymine and 2 equivalents of $K_2CO_3$ are stirred for 5 minutes in absolute DMF at room temperature.

Compound (9) (1.18 g; 3.36 mmol), dissolved in absolute DMF, is subsequently added dropwise and the mixture is stirred for 4 hours at 60° C. After the reaction has ended, the DMF is distilled off, and the crude product is covered with a layer of ethyl acetate. The organic phase is extracted 3 times in each case by shaking in succession with 20 ml of 1N HCl, saturated NaHCO$_3$ and saturated NaCl solution. The organic phase is separated off, dried using Na$_2$SO$_4$ and evaporated to dryness. The product is finally chromatographed on silica gel using ethyl acetate/n-hexane 2:1 as the eluent.

Yield: 650 mg (50%) Rf: 0.53 Eluent: ethyl acetate/n-hexane 2:1 M.p.: 184 to 187° C.

Example 12

4-(Thymin-1-yl) -2-L-aminobutyric acid* TFA

Compound (11) in TFA (2 ml per mmol) is treated for 2 hours in an ultrasonic bath. The solution obtained is subsequently pipetted into absolute ether, during which process the TFA salt precipitates. The TFA salt obtained is filtered off and dried over KOH under an oil-pump vacuum.

Yield: quantitative.

Example 13

4-(Thymin-1-yl) -2-L-aminobutyric acid* HBr

Compound (11) is dissolved in HBr/acetic acid (5 ml per mmol), and the solution is stirred for 30 minutes at room temperature. The solution is subsequently pipetted into absolute ether, during which process the HBr salt precipitates. The HBr salt obtained is filtered off and dried over KOH under an oil-pump vacuum.

Yield: quantitative. M.p.: >200° C., decomposition

Example 14

N-Boc-4-(thymin-1-yl)-2-L-aminobutyric acid (12)

Starting from the TFA salt of Example 12, the Boc protective group is introduced in the same manner as described for the HBr salt of Example 13. The introduction of protective groups is described by way of example, starting from the HBr salt.

The HBr salt (10.7 g; 34.7 mmol) is introduced into THF. The pH of the solution is brought to 8 by adding triethylamine. 1.1 equivalents of di-tert-butyl dicarbonate, dissolved in THF, are then added dropwise, and the mixture is stirred overnight at room temperature. During the reaction, care is taken that the pH does not drop below a value of 8. After the reaction has ended, the THF is distilled off, the residue is covered with a layer of ethyl acetate, and the pH is brought to 1 to 2 by adding 1N HCl. The phases are then separated, and the organic phase is dried over Na$_2$SO$_4$ and evaporated to dryness. The crude product obtained is chromatographed on silica gel using CH$_2$Cl$_2$/MeOH/HOAc 90:10:1.

Yield: 6 g (53%) Rf: 0.53 Eluent CH$_2$Cl$_2$/MeOR/HOAc 80:20:1 M.p.: 124° C.

Example 15

N-Fmoc-4-(thymin-1-yl)-2-L-aminobutyric acid

The TFA salt of Example 12 (3.4 g; 9.66 mmol) is dissolved in a solvent mixture of acetone/water (30 ml : 30 ml), and 2 equivalents of NaHCO$_3$ are added. 1 equivalent of 9-fluorenylmethyl-succinimidyl carbonate is then added, and the mixture is stirred overnight at room temperature. After the reaction has ended, the acetone is distilled off, chloroform is added to the aqueous phase, and this is subsequently acidified with 1N HCl to bring the pH to 2. The phases are then separated. Finally, the chloroform phase is extracted 3 times by shaking with in each case 50 ml of 0.1N HCl, saturated NaHCO$_3$ and saturated NaCl solution. The phases are separated. The organic phase is dried over Na$_2$SO$_4$ and then evaporated to dryness. The product is subjected to column chromatography on silica gel using CH$_2$Cl$_2$/MeOH/HOAc 90:10:1 as the eluent.

Yield: 2.7 g (55.3%) Rf: 0.80 Eluent: CH$_2$Cl$_2$/MeOH/HOAc 80:20:1

Example 16 tert-Butyl N-Boc-4-(N$_4$-benzoyl-cytosin-1-yl)-2-L-amino-butyrate 2 equivalents of N$^4$-benzoyl-cytosine and 2 equivalents of K$_2$CO$_3$ are stirred for 5 minutes in absolute DMF at room temperature. Compound (9) (13.35 g; 37.8 mmol), dissolved in DMF, is then added dropwise. The solution is heated to 60° C. and stirred for 4 hours at this temperature. After the reaction has ended, the DMF is distilled off, the residue is covered with a layer of ethyl acetate, and the mixture is extracted 3 times in each case by shaking in succession with 100 ml of 1N HCl, saturated NaHCO$_3$ and saturated NaCl solution. Finally, the organic phase is dried over Na$_2$SO$_4$ and evaporated to dryness. The crude product obtained is chromatographed on silica gel using ethyl acetate/n-hexane 1:1.

Yield: 6.1 g (35%) Rf: 0.55 Eluent: CH$_2$Cl$_2$/MeOH 9:1

Example 17

4-(N$_4$-Benzoyl-cytosin-1-yl) -2-L-aminobutyric acid* TFA tert-Butyl N-Boc-4-(N$_4$-benzoyl-cytosin-1-yl)-2-L-amino-butyrate in TFA (2 ml per mmol) is treated for 2 hours in an ultrasonic bath. The solution obtained is subsequently is pipetted into absolute ether, during which process the TFA salt precipitates. The TFA salt obtained is filtered off and dried over KOH under an oil-pump vacuum.

Yield: quantitative.

Example 18

N-Boc-4-(N$_4$-benzoyl-cytosin-1-yl) -2-L-aminobutyric acid

The TFA salt (5.5 g; 10.43 mmol) of Example 17 is dissolved in a solvent mixture of dioxane/water (25 ml : 15 ml), and 3 equivalents of Na$_2$CO$_3$ are added. The solution is stirred for 5 minutes at room temperature. 1.3 equivalents of di-tert-butyl dicarbonate, dissolved in 15 ml of dioxane, are subsequently added dropwise and the mixture is stirred overnight at room temperature. After the reaction has ended, the dioxane is distilled off, and the aqueous phase is covered with a layer of ethyl acetate, and acidified with 1N HCl to bring the pH to 2. The phases are then separated, and the organic phase is extracted 3 times by shaking in succession with in each case 100 ml of 1N HCl, saturated NaHCO$_3$ and saturated NaCl solution. The organic phase is dried over Na$_2$SO$_4$ and then evaporated to dryness. The product is precipitated from ethyl acetate/n-hexane.

Yield: 3.65 g (83%). Rf: 0.50 Eluent: CH$_2$Cl$_2$/MeOH/HOAc 80:20:1

Example 19 tert-Butyl N-Boc-4-($N_4$-Z-cytosin-1-yl)-2-L-aminobutyrate $N_4$-Z-Cytosine (2 equivalents) is introduced into absolute DMF, and 2 equivalents of $K_2Co_3$ are added. The mixture is stirred for 5 minutes at room temperature. The mesylate (9) (11 g; 31.1 mmol), dissolved in DMF, is then added dropwise. After the addition has ended, the mixture is heated to 60° C. and stirred for 4 hours at this temperature. After the reaction has ended, the DMF is distilled off, the residue is covered with a layer of ethyl acetate, and the mixture is extracted 3 times by shaking in succession with in each case 100 ml of 1N HCl, saturated $NaHCO_3$ and saturated NaCl solution. The organic phase is dried over $Na_2SO_4$ and then evaporated to dryness. Finally, the crude product obtained is chromatographed on silica gel using ethyl acetate/n-hexane 1:1 as the eluent.

Yield: 9 g; (57.6%) Rf: 0.21 Eluent: ethyl acetate/n-hexane 2:1

Example 20

4-($N^4$-Z-Cytosin-1-yl)-2-L-aminobutyric acid* TFA tert-Butyl N-Boc-4-($N_4$-Z-cytosin-1-yl)-2-L-aminobutyrate (9 g; 18.9 mmol) in TFA (2 ml per mmol) is treated for 2 hours in an ultrasonic bath. The solution obtained is subsequently pipetted into absolute ether, during which process the TFA salt precipitates. The TFA salt obtained is filtered off and dried over KOH under an oil-pump vacuum.

Yield: quantitative.

Example 21

N-Boc-4-($N_4$-Z-cytosin-1-yl)-2-L-aminobutyric acid

The TFA salt (6.74 g; 14.6 mmol) of Example 20 is dissolved in a solvent mixture of dioxane/water (2:1), and 3 equivalents of $Na_2CO_3$ are added. The solution is stirred for 5 minutes at room temperature. 1.3 equivalents of ditert-butyl dicarbonate, dissolved in a little dioxane, are subsequently added dropwise, and the mixture is stirred overnight at room temperature. After the reaction has ended, the dioxane is distilled off, and the aqueous phase is covered with a layer of ethyl acetate and acidified with 1N HCl to bring the pH to 2. The phases are then separated, and the organic phase is extracted 3 times by shaking in succession with in each case 100 ml of 1N HCl, saturated $NaHCO_3$ and saturated NaCl solution. The organic phase is dried over $Na_2SO_4$ and then evaporated to dryness. The product is precipitated from ethyl acetate/n-hexane.

Yield: 4 g; (61.4%) Rf: 0.85 Eluent: $CH_2Cl_2$/MeOH/HOAc 80:20:1z M.p.: 190° C.

Example 22

Methyl 2S,4S-N-Boc-4-($N^3$-benzoyl-thymin-1-yl)-pyrrolidine-2-carboxylate (16)

2.5 equivalents of triphenylphosphine and 2.5 equivalents of DEAD are dissolved in absolute THF and the mixture is stirred for 5 minutes at room temperature. After this time, the $N^3$-benzoyl-thymine (2 equivalents) is added, and the mixture is stirred for another 5 minutes at room temperature. 2S,4R-N-Boc-hydroxyproline methyl ester (1.23 g; 5 mmol), which has been dissolved in absolute DMF, is subsequently added dropwise and the mixture is stirred overnight at room temperature. After the reaction has ended, the DMF is distilled off and the crude product is chromatographed on silica gel using ethyl acetate/n-hexane 1:1 as the eluent.

Yield: 1.2 g (52.5%) Rf: 0.40 Eluent: ethyl acetate/n-hexane 2:1

Example 23

Benzyl 2S,4S-N-Boc-4-($N^3$-benzoyl-thymin-1-yl) pyrrolidine-2-carboxylate (15)

2.5 equivalents of triphenylphosphine and 2.5 equivalents of DEAD are dissolved in absolute THF and the mixture is stirred for 5 minutes at room temperature. After this time, the $N^3$-benzoyl-thymine (2 equivalents) is added, and the mixture is stirred for another 5 minutes at room temperature. 2S,4R-N-Boc-hydroxyproline benzyl ester (11 g; 34.3 mmol), which has been dissolved in absolute DMF, is subsequently added dropwise and the mixture is stirred overnight at room temperature. After the reaction has ended, the DMF is distilled off and the crude product is chromatographed on silica gel using ethyl acetate/n-hexane 1:1 as the eluent.

Yield: 10.86 g (58.3%) Rf: 0.68 Eluent ethyl acetate/n-hexane 2:1

Example 24a 2S,4S-N-Boc-4-($N^3$-benzoyl-thymin-1-yl)-pyrrolidine-2-carboxylic acid Methyl 2S,4S-N-Boc-4-($N^3$-benzoyl-thymin-1-yl)-pyrrolidine-2-carboxylate (5.8 g; 12.7 mmol) is dissolved in isopropanol, and 1.1 equivalents of 1N NaOH are added. The mixture is subsequently stirred at room temperature. After the reaction has ended (TLC check, eluent $CH_2Cl_2$/MeOH/HOAc 90:10:1), the isopropanol is distilled off, and the residue is covered with a layer of ethyl acetate and acidified with 1N HCl to bring the pH to 1. The phases are then separated, and the organic phase is dried over $Na_2SO_4$ and then evaporated to dryness. The crude product obtained in this manner is reacted further without further purification (see Example 25).

Rf: 0.60 Eluent: $CH_2Cl_2$/MeOH 9:1

Example 24b 2S,4S-N-Boc-4-($N^3$-benzoyl-thymin-1-yl)-pyrrolidine-2-carboxylic acid Benzyl 2S,4S-N-Boc-4-($N^3$-benzoyl-thymin-1-yl)-pyrrolidine-2-carboxylate (10.86 g; 20.3 mmol) is dissolved in MeOH, and the reaction vessel is purged for 10 minutes with $N_2$. After dry catalyst (Pd on active charcoal 10%) has been added, the mixture is hydrogenated in a weak stream of hydrogen under atmospheric pressure. After the reaction has ended (TLC check, $CH_2Cl_2$/MeOH/HOAc 90:10:1), the catalyst is removed by filtration and washed thoroughly. The filtrate is evaporated to dryness and dried on an oil-pump.

Yield: 9.03 g (quantitative). Rf: 0.60 Eluent: $CH_2Cl_2$/MeOH 9:1

Example 25

2S,4S-N-Boc-4-(thymin-1-yl)pyrrolidine-2-carboxylic acid (17)

2S,4S-N-Boc-4-($N^3$-benzoyl-thymin-1-yl) -pyrrolidine-2-carboxylic acid (9.03 g; 20.3 mmol) and $NH_3$ in methanol are stirred overnight at room temperature. The solvent is then distilled off. The crude product obtained is subjected to column chromatography on silica gel using $CH_2Cl_2$/MeOH/HOAc 90:10:1 as the eluent.

Yield: 3.55 g (51.7%) Rf: 0.33 Eluent: $CH_2Cl_2$/MeOH/HOAc 80:20:1M.p.: 228° C.

Example 26

Benzyl 2S,4S-N-Boc-4-($N^4$-benzoyl-cytosin-1-yl)-pyrrolidine-2-carboxylate 2.5 equivalents of triphenylphosphine and 2.5 equivalents of DEAD are dissolved in absolute THF and the mixture is stirred for 5 minutes at room temperature. After this time, $N^3$-benzoyl-thymine (2 equivalents) is added and the mixture is stirred for another 5 minutes at room temperature. 2S,4R-N-Boc-hydroxyproline methyl ester (7.5 g; 23.36 mmol), which has been dissolved in absolute DMF, is subsequently added dropwise and the mixture is stirred overnight at room temperature. After the reaction has ended, the DMF is distilled off, and the crude product is chromatographed on silica gel using ethyl acetate/n-hexane 1:1 as the eluent.

Yield: 5.6 g (47.2%) Rf: 0.56 Eluent: ethyl acetate/n-hexane 2:1

Example 27

2S,4S-N-Boc-4-($N^4$-benzoyl-cytosin-1-yl)-pyrrolidine-2-carboxylic acid

Benzyl 2S,4S-N-Boc-4-($N^4$-benzoyl-cytosin-1-yl)-pyrrolidine-2-carboxylate (1.9 g; 3.75 mmol) is dissolved in MeOH and the reaction vessel is purged with $N_2$ for 10 minutes. After dry catalyst (Pd on active charcoal 10%) has been added, the mixture is hydrogenated in a weak stream of hydrogen under atmospheric pressure. After the reaction has ended (TLC check, $CH_2Cl_2$/MeOH/HOAc 90:10:1), the catalyst is removed by filtration and washed thoroughly. The filtrate is evaporated to dryness and dried on an oil-pump.

Yield: 1.51 g (96.8%) Rf: 0.05 Eluent: $CH_2Cl_2$/MeOH 9:1

Example 28

2S,4S-N-Boc-4-(N-benzoyl-cytosin-1-yl)-pyrrolidine-2-carboxyglycine benzyl ester 2S,4S-N-Boc-4-($N^4$-benzoyl-cytosin-1-yl)-pyrrolidine-2-carboxylic acid (5.9 g; 14.2 mmol) is introduced into DMF, and the solution is cooled to −30° C. 1.3 equivalents of HOBt followed by 1.3 equivalents of EDCI*HCl are added at this temperature and the mixture is stirred for 10 to 15 minutes at not more than −15° C. In the meantime, glycine benzyl ester hydrochloride (1.2 equivalents) is taken up in DMF and neutralized with N-ethylmorpholine. After the preactivation time, this solution is added dropwise to the reaction solution which has been cooled to −15° C. The mixture is stirred for 1 hour at not more than −10C and subsequently overnight at room temperature. After the reaction has ended, the DMF is distilled off, and the residue is covered with a layer of ethyl acetate and extracted 3 times by shaking with in each case 100 ml of 1N HCl, saturated $NaHCO_3$ and saturated NaCl solution. The organic phase is dried over $Na_2SO_4$ and then evaporated to dryness. Finally, the crude product is chromatographed on silica gel using ethyl acetate/n-hexane 2:1.

Yield: 4.2 g (51.2%) Rf: 0.25 Eluent: ethyl acetate/n-hexane 2:1

Example 29

2S,4S-N-Boc-4-($N^4$-benzoyl-cytosin-1-yl)-pyrrolidine-2-carboxyglycine 2S,4S-N-Boc-4-($N^4$-benzoyl-cytosin-1-yl)-pyrrolidine-2-carboxyglycine benzyl ester (3.67 g; 6.38 mmol) is dissolved in MeOH and the reaction vessel is purged with $N_2$ for 10 minutes. After dry catalyst (Pd on active charcoal 10%) has been added, the mixture is hydrogenated in a weak stream of hydrogen under atmospheric pressure. After the reaction has ended (TLC check, $CH_2Cl_2$/MeOH/HOAc 90:10:1), the catalyst is removed by filtration and washed thoroughly. The filtrate is evaporated to dryness and dried on an oil-pump.

Yield: 2.78 g (89.7%)

Example 30

Methyl 2S,4S-N-Boc-4-($N^4$-Z-cytosin-1-yl)-pyrrolidine-2-carboxylate 2.5 equivalents of triphenylphosphine and 2.5 equivalents of DEAD are dissolved in absolute THF and the mixture isstirred for 5 minutes at room temperature. After this time, NZ-cytosine (2 equivalents) is added and the mixture is stirred for another 5 minutes at room temperature. 2S,4R-N-Boc-hydroxyproline methyl ester (10 g; 40.8 mmol), which has been dissolved in absolute DMF, is subsequently added dropwise and stirred overnight at room temperature. After the reaction has ended, the DMF is distilled off, and the crude product is chromatographed on silica gel using ethyl acetate/n-hexane 1:1 as the eluent.

Yield: 15.6 g (81%) Rf: 0.60 Eluent: ethyl acetate/n-hexane 2:1

Example 31

2S,4S-N-Boc-4-($N^4$-Z-cytosin-1-yl)-pyrrolidine-2-carboxylic acid

Methyl 2S,4S-N-Boc-4-($N^4$-Z-cytosin-1-yl)-pyrrolidine-2-carboxylate (15.6 g; 33 mmol) is dissolved in isopropanol, and 1.1 equivalents of 1N NaOH are added. The mixture is subsequently stirred at room temperature. After the reaction has ended (TLC check, eluent $CH_2Cl_2$/MeOH/HOAc 90:10:1), the isopropanol is distilled off, and the residue is covered with a layer of ethyl acetate and acidified with 1N HCl to bring the pH to 1. The phases are then separated, and the organic phase is dried over $Na_2SO_4$ and then evaporated to dryness. The crude product obtained in this manner is chromatographed on silica gel using $CH_2Cl_2$/MeOH/HOAc 90:10:1 as the eluent.

Yield: 7.27 g (48%) Rf: 0.73 Eluent: $CH_2Cl_2$/MeOH/HOAc 80:20:1

Example 32

Methyl 2S,4S-N-Boc-4-(4-nitro-benzoyloxy)-pyrrolidine-2-carboxylate (18)

2S,4R-N-Boc-hydroxyproline methyl ester (60.05 g; 269 mmol), 1.2 equivalents of triphenylphosphine (85.93 g; 327 mmol) and 1.25 equivalents of para-nitro-benzoic acid (56.05 g; 335 mmol) are dissolved in absolute THF under protective gas. The solution obtained is cooled to 0° C. Diethyl azodicarboxylate, dissolved in absolute THF, is added dropwise at this temperature. The mixture is subsequently allowed to thaw to room temperature and is subsequently stirred at room temperature for a further 70 hours. The solvent is then distilled off and the residue is treated with ether. By-products which precipitate in the process are filtered off with suction, the filtrate is concentrated on a rotary evaporator, and the crude product obtained is subjected to a first purification step on silica gel using ethyl acetate/n-hexane (in a ratio of 2:1) and finally subjected to a final purification by chromato-graphy on silica gel using $CH_2Cl_2$/MeOH (in a ratio of 60:1).

Yield: 100 g (94.15%) Rf: 0.85 Eluent: ethyl acetate/n-hexane 2:1

Example 33

2S,4S-N-Boc-hydroxyproline methyl ester (19)

Methyl 2S,4S-N-Boc-4-(4-nitro-benzoyloxy)-pyrrolidine-2-carboxylate (11.82 g; 30 mmol) is dissolved in approximately 300 ml of absolute MeOH. A solution of sodium methylate (1.62 g; 30 mmol) in methanol is added dropwise to this solution and the mixture is stirred for 30 minutes at room temperature. The pH is subsequently brought to 5 using 1N HCl. The methanol is then distilled off. The aqueous phase is extracted repeatedly using ethyl acetate, and the combined organic phases are finally washed with saturated NaCl solution, dried over sodium sulphate and then evaporated to dryness. The crude product obtained is chromatographed on silica gel using ethyl acetate/n-hexane (in a ratio of 2:1).

Yield: 6.98 g (94.9%) Rf: 0.35 Eluent: ethyl acetate/n-hexane 2:1

Example 34

Methyl 2S,4R-N-Boc-4-($N^3$-benzoyl-thymin-1-yl)-pyrrolidine-2-carboxylate (20)

2.5 equivalents of triphenylphosphine and 2.5 equivalents of DEAD are dissolved in absolute THF and the mixture is stirred for 5 minutes at room temperature. After this time, $N^3$-benzoyl-thymine (2 equivalents) is added and the mixture is stirred for another 5 minutes at room temperature. 2S,4S-N-Boc-hydroxyproline methyl ester (30 g; 122 mmol), which has been dissolved in absolute DMF, is subsequently added dropwise and stirred overnight at room temperature. After the reaction has ended, the DMF is distilled off, and the crude product is chromatographed on silica gel using ethyl acetate/n-hexane 1:1 as the eluent.

Yield: 38.0 g (67.9%) Rf: 0.27 Eluent: ethyl acetate/n-hexane 1:1

Example 35

2S,4R-N-Boc-4-($N^3$-benzoyl-thymin-1-yl)-pyrrolidine-2-carboxylic acid

Methyl 2S,4R-N-Boc-4-($N^3$-benzoyl-thymin-1-yl)-pyrrolidine-2-carboxylate (38 g; 83 mmol) is dissolved in isopropanol, and 1.1 equivalents of 1N NaOH are added. The mixture is subsequently stirred at room temperature. After the reaction has ended (TLC check, eluent $CH_2Cl_2$/MeOH/HOAc 90:10:1), the isopropanol is distilled off, and the residue is covered with a layer of ethyl acetate and acidified with 1N HCl to bring the pH to 1. The phases are then separated, and the organic phase is dried over $Na_2SO_4$ and then evaporated to dryness. The crude product obtained in this manner is reacted further without further purification (see Example 36).

Example 36

2S, 4R-N-Boc-4-(thymin-1-yl) -pyrrolidine-2-carboxylic acid (21)

2S,4R-N-Boc-4-($N^3$-benzoyl-thymin-1-yl) -pyrrolidine-2-carboxylic acid is stirred with ammonia in methanol overnight at room temperature. The solvent is then distilled off. The crude product obtained is subjected to column chromatography on silica gel using $CH_2Cl_2$/MeOH/HOAc 90:10:1 as the eluent.

Yield: 12.6 g (44.8%) Rf: 0.25 Eluent $CH_2Cl_2$/MeOH/HOAc 90:10:1

Example 37

Methyl 2S,4R-N-Boc-N-($N^4$-benzyloxycarbonylcytosin-1-yl)-pyrrolidine-2-carboxylate 3.28 g (12.5 mmol) of triphenylphosphine and 2.18 g (12.5 mmol) of DEAD are dissolved in 20 ml of absolute THF and the mixture is stirred for 5 minutes at room temperature. After this time, 2.45 g (10 mmol) of $N^4$-benzyloxycarbonylcytosine are added and the mixture is stirred for a further 5 minutes. 1.23 g (5 mmol) of N-Boc-L-cis-hydroxyproline methyl ester, dissolved in DMF, are subsequently added dropwise and the mixture is stirred overnight at room temperature. The DMF is distilled off, and ethyl acetate is added to the residue. The mixture is now extracted once by shaking with saturated NaCl solution, and the organic phase is dried over $Na_2SO_4$, filtered and concentrated. The residue is chromatographed on $SiO_2$ using methylene chloride/methanol 30:1 as the eluent.

Yield: 840 mg (35% of theory) Rf: 0.7 Eluent $CH_2Cl_2$/$CH_3OH$ 30:1

Example 38

2S,4R-N-Boc-4-($N^4$-benzyloxycarbonylcytosin-1-yl) -pyrrolidine-2-carboxylic acid 580 mg (1.2 mmol) of methyl 2S,4R-N-Boc-4-($N^4$-benzyloxy-carbonylcytosin-1-yl) -pyrrolidine-2-carboxylate are dissolved in 10 ml of dioxane and 2 ml of $H_2O$, and the solution is cooled to 10° C. 1.2 ml (1.2 mmol) of 1N NaOH are now added dropwise at 10° C. and, after 5 hours, another 0.6 ml (0.6 mmol) of 1N NaOH at the same temperature. The mixture is stirred for a further 2 hours at 10° C. and allowed to stand overnight in a refrigerator. The solution is concentrated, ethyl acetate is added, and the mixture is extracted once by shaking with 1N HCl. The organic phase is then dried over $Na_2SO_4$, filtered and concentrated. The residue is chromatographed on silica gel using $CH_2Cl_2$/$CH_3OH$ 10:1 as the eluent.

Yield: 300 mg (53.0% of theory) Rf: 0.17 Eluent $CH_2Cl_2$/$CH_{30}OH$ 10:1

Example 39

Methyl 2R,4S-N-Boc-4-($N^3$-benzoyl-thymin-1-yl)-pyrrolidine-2-carboxylate 69.5 (265 mmol) of triphenylphosphine and 46.1 g (265 mmol) of DEAD are dissolved in 400 ml of absolute THF, and the solution is stirred for 5 minutes at room temperature. After this time, 48.8 g (212 mmol) of $N^3$-benzoyl-thymine are added, and the mixture is stirred at room temperature for another 5 minutes. 26.0 g (106 mmol) of N-Boc-D-trans-hydroxyproline methyl ester, dissolved in DMF, are subsequently added dropwise and the mixture is stirred overnight at room temperature. After the reaction has ended, the DMF is distilled off, and the residue is taken up in ethyl acetate and extracted once by shaking with saturated NaCl solution. The organic phase is dried over $Na_2SO_4$, filtered and concentrated. The crude product is chromatographed on silica gel using ethyl acetate/n-hexane 1:1 as the eluent.

Yield: 22.58 g (46.5% of theory) Rf: 0.26 Eluent ethyl acetate/n-hexane 1:1

Example 40

2R,4S-N-Boc-4-(thymin-1-yl)-pyrrolidine-2-carboxylic acid 1.18 g (2.5 mmol) of methyl 2R,4S-N-Boc-4-($N^3$-benzoyl-thymin-1-yl)-pyrrolidine-2-carboxylate are dissolved in 20 ml of isopropanol and 10 ml of dioxane and the solution is cooled to 3° C. 5 ml (5 mmol) of 1N NaOH are then added dropwise at 3° C., and the mixture is stirred for 7 hours at this temperature. Another 2.5 ml (2.5 mmol) of 1N NaOH are subsequently added dropwise, and the mixture is left to stand overnight in an ice-bath. The solution is concentrated, ethyl acetate is added, and 1N HCl is added until the pH has been brought to 1. The mixture is now extracted once by shaking with ethyl acetate, and the organic phase is dried over $Na_2SO_4$ and concentrated to dryness. The crude product is chromatographed on silica gel using $CH_2Cl_2/CH_3OH/HOAc$ 90:10:1 as the eluent.

Yield: 430 mg (49.1% of theory) Rf: 0.23 Eluent $CH_2Cl_2/CH_3OH/HOAc$ 90:10:1

Example 41

N-Boc-4-(thymin-1-yl)-2-L-aminobutyryl-glycine methyl ester

N-Boc-4-(thymin-1-yl)-2-L-aminobutyric acid (6.0 g; 18.35 mmol) is introduced into DMF, and the solution is cooled to -30° C. 1.3 equivalents of HOBt followed by 1.3 equivalents of EDCI*HCl are added at this temperature, and the mixture is stirred for 10 to 15 minutes at not more than -15° C. In the meantime, glycine methyl ester hydrochloride (1.2 equivalents) is taken up in DMF and neutralized with N-ethylmorpholine. After the preactivation time, this solution is added dropwise to the reaction solution which has been cooled to -15° C. The mixture is stirred for 1 hour at not more than -10° C. and subsequently overnight at room temperature. After the reaction has ended, the DMF is distilled off, and the residue is covered with a layer of ethyl acetate and extracted 3 times by shaking with in each case 100 ml of 1N HCl, saturated $NaHCO_3$ and saturated NaCl solution. The organic phase is dried over $Na_2SO_4$ and then evaporated to dryness. Finally, the crude product is chromatographed on silica gel using ethyl acetate/n-hexane 2:1.

Yield: 3.9 g (53%) Rf: 0.56 Eluent: $CH_2Cl_2/MeOH$ 9:1

Example 42

N-Boc-4-(thymin-1-yl)-2-L-aminobutyryl-glycine (3.9 g; 10.1 mmol) is dissolved in isopropanol, and 1.1 equivalents of 1N NaOH are added. The mixture is subsequently stirred at room temperature. After the reaction has ended (TLC check, eluent $CH_2Cl_2/MeOH/HOAc$ 90:10:1), the isopropanol is distilled off, and the residue is covered with a layer of ethyl acetate and acidified with 1N HCl to bring the pH to 1. The phases are then separated, and the organic phase is dried over $Na_2SO_4$ and then evaporated to dryness. The residue is subsequently covered with a layer of ethyl acetate and acidified with 1N HCl. After phase separation, the organic phase is dried over $Na_2SO_4$ and then evaporated to dryness.

Yield: 3.1 g (82%)

Example 43

2S,4S-N-Boc-4-(thymin-1-yl) -pyrrolidine-2-carboxy-glycine benzyl ester 2S,4S-N-Boc-4-(thymin-1-yl)-2-carboxylic acid (5.0 g; 14.7 mmol) is introduced into DMF and the solution is cooled to -30° C. 1.3 equivalents of HOBt followed by 1.3 equivalents of EDCI*HCl are added at this temperature and the mixture is stirred for 10 to 15 minutes at not more than -15° C. In the meantime, glycine benzyl ester hydrochloride (1.2 equivalents) is taken up in DMF and neutralized with N-ethylmorpholine. After the preactivation time, this solution is added dropwise to the reaction solution which has been cooled to -15° C. The mixture is stirred for 1 hour at not more than -10° C. and subsequently overnight at room temperature. After the reaction has ended, the DMF is distilled off, and the residue is covered with a layer of ethyl acetate and extracted 3 times by shaking with in each case 100 ml of 1N HCl, saturated $NaHCO_3$ and saturated NaCl solution. The organic phase is dried over $Na_2SO_4$ and then evaporated to dryness. Finally, the crude product is chromatographed on silica gel using $CH_2Cl_2/MeOH$ (in a ratio of 95:5). For further purification, the product, which is quite pure already, is precipitated from a mixture of ethyl acetate, ether and n-hexane.

Yield: 3.7 g (51.8%) Rf: 0.67 Eluent: $CH_2Cl_2/MeOH$ 9:1 M.p.: 178° C.

Example 44

2S, 4S-N-Boc-4-(thymin-1-yl) -pyrrolidine-2-carboxy-glycine 2S, 4S-N-Boc-4-(thymin-1-yl) -pyrrolidine-2-carboxy-glycine benzyl ester (3.7 g; 7.61 mmol) is dissolved in MeOH, and the reaction vessel is purged with $N_2$ for 10 minutes. After dry catalyst (Pd on active charcoal 10%) has been added, the mixture is hydrogenated in a weak stream of hydrogen under atmospheric pressure. After the reaction has ended (TLC check, $CH_2Cl_2/MeOH/HOAc$ 90:10:1), the catalyst is filtered off and washed thoroughly. The filtrate is evaporated to dryness and dried on an oil-pump.

Yield: 2.7 g (89.5%)

Example 45

2S,4R-N-Boc-4-(thymin-1-yl)-pyrrolidine-2-carboxyglycine benzyl ester 2S,4R-N-Boc-4-(thymin-1-yl)-pyrrolidine-2-carboxylic acid (4.65 g; 13.7 mmol) is introduced into DMF and the solution is cooled to -30° C. 1.3 equivalents of HOBt followed by 1.3 equivalents of EDCI*HCl are added at this temperature and the mixture is stirred for 10 to 15 minutes at not more than -15° C. In the meantime, glycine benzyl ester hydrochloride (1.2 equivalents) is taken up in DMF and neutralized with N-ethylmorpholine. After the preactivation time, this solution is added dropwise to the reaction solution which has been cooled to -15° C. The mixture is stirred for 1 hour at not more than -10° C. and subsequently overnight at room temperature. After the reaction has ended, the DMF is distilled off, and the residue is covered with a layer of ethyl acetate and extracted 3 times by shaking with in each case 100 ml of 1N HCl, saturated $NaHCO_3$ and saturated NaCl solution. The organic phase is dried over $Na_2SO_4$ and then evaporated to dryness.

Yield: 6.7 g (97.6%) Rf: 0.56 Eluent: $CH_2Cl_2/MeOH$ 9:1

Example 46

2S, 4R-N-Boc-4-(thymin-1-yl) -pyrrolidine-2-carboxy-glycine 2S,4R-N-Boc-4-(thymin-1-yl) -pyrrolidine-2-carboxy-glycine benzyl ester (6.0 g; 12.3 mmol) is dissolved in MeOH, and the reaction vessel is purged with $N_2$ for 10 minutes. After dry catalyst (Pd on active charcoal 10%) has been added, the mixture is hydrogenated in a weak stream of hydrogen under atmospheric pressure. After the reaction has ended (TLC check, $CH_2Cl_2$/MeOH/HOAc 90:10:1), the catalyst is filtered off and washed thoroughly. The filtrate is evaporated to dryness and dried on an oil-pump.

Yield: 3.7 g (75.8%) Rf: 0.25 Eluent: $CH_2Cl_2$/MeOH/HOAc 90:10:1

Olipomers

Example 47

Solid-phase synthesis of H—(IT)$_3$—Gly—OH 120 mg (0.1 mmol) of tert-butyloxycarbonyl-glycine-PAM resin are introduced into the reaction vessel. Prior to each coupling step, the tert-butyloxycarbonyl protective group is cleaved off by treatment with trifluoroacetic acid. In each case 136 mg (0.34 mmol) of IBocT are activated by reaction with 365 mg (2.7 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25-minute treatment with a solution of 200 µl of trifluoromethanesulphonic acid in 2 ml of trifluoroacetic acid. Purification is effected by RP-HPLC on C8 using an ascending gradient of TFA in acetonitrile.

Yield: 27 mg (29%)

Example 48

Solid-phase synthesis of H—(IT)$_7$—Gly—OH 120 mg (0.1 mmol) of tert-butyloxycarbonyl-glycine-PAM resin are introduced into the reaction vessel. Prior to each coupling step, the tert-butyloxycarbonyl protective group is cleaved off by treatment with trifluoroacetic acid. In each case 136 mg (0.34 mmol) of IBocT are activated by reaction with 365 mg (2.7 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25-minute treatment with a solution of 200 µl of trifluoromethanesulphonic acid in 2 ml of trifluoroacetic acid. Purification is effected by RP-HPLC on C8 using an ascending gradient of TFA in acetonitrile.

Yield: 72 mg (36%)

Example 49

Solid-phase synthesis of H—(IT)$_{15}$—Gly—OH 120 mg (0.1 mmol) of tert-butyloxycarbonyl-glycine-PAM resin are introduced into the reaction vessel. Prior to each coupling step, the tert-butyloxycarbonyl protective group is cleaved off by treatment with trifluoroacetic acid. In each case 136 mg (0.34 mmol) of IBocT are activated by reaction with 365 mg (2.7 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25-minute treatment with a solution of 200 µl of trifluoromethanesulphonic acid in 2 ml of trifluoroacetic acid. Purification is effected by RP-HPLC on C8 using an ascending gradient of TFA in acetonitrile.

Yield: 80 mg (19%) LDI-MS: found: 4282 g/mol, calculated 4279.2 g/mol LDI: Laser desorption ionization Example 50

Solid-phase synthesis of H—(IC)$_2$—Gly—OH 120 mg (0.1 mmol) of tert-butyloxycarbonyl-glycine-PAM resin are introduced into the reaction vessel. Prior to each coupling step, the tert-butyloxycarbonyl protective group is cleaved off by treatment with trifluoroacetic acid. In each case 166 mg (0.34 mmol) of IBocCB$^{Bz}$ are activated by reaction with 365 mg (2.7 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25-minute treatment with a solution of 200 µl of trifluoromethanesulphonic acid in 2 ml of trifluoroacetic acid. Cleavage of the benzoyl protective group is effected by the action of concentrated ammonia solution at 55C. Purification is effected by RP-HPLC on C8 using an ascending gradient of TFA in acetonitrile.

Yield: 7 mg (11%) FAB: Fast atom bombardment FAB-MS: found: 605 g/mol, calculated: 605 g/mol Example 51

Solid-phase synthesis of H—(IIT-Ala)$_2$—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 164 mg (0.05 mmol) of IIBocT and 189 mg (1.0 mmol) of tert-butyloxycarbonyl-alanine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25- minute treatment with a solution of 200 µl of trifluoromethanesulphonic acid in 2 ml of trifluoroacetic acid. Purification is effected by RP-HPLC on C8 using an ascending gradient of TFA in acetonitrile.

Yield: 34 mg (59%) FAB-MS: found: 578 g/mol, calculated: 578.6 g/mol

Example 52

Solid-phase synthesis of H—(IIT—Ala)$_2$—OH 192 mg (0.1 mmol) of N-fluorenylmethoxycarbonyl-alanine-HMP resin are introduced into the reaction vessel. Prior to each coupling step, the N-fluorenylmethoxycarbonyl protective group is cleaved off by treatment with piperidine. In each case 218 mg (0.5 mmol) of IIFmocT and 311 mg (1.0 mmol) of N-fluorenylmethoxycarbonyl-alanine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the N-fluorenylmethoxycarbonyl protective group is removed by treatment with piperidine. Cleavage from the support is effected by 60-minute treatment with trifluoroacetic acid. Purication is effected by RP-HPLC on C8 using an ascending gradient of TFA in acetonitrile.

Yield: 27 mg (47%)

Example 53

Solid-phase synthesis of H—(IIC—Ala)$_2$—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 213 mg (0.5 mmol) of IIBocC$^{Bz}$ and 189 mg (1.0 mmol) of tert-butyloxycarbonyl-alanine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25-minute treatment with a solution of 200 µl of trifluoromethanesulphonic acid in 2 ml of trifluoroacetic acid. Cleavage of the benzoyl protective group is effected by the action of 0.4M aqueous/methanolic sodium hydroxide solution for 16 hours at room temperature. Purification is effected by RP-HPLC on C8 using an ascending gradient of TFA in acetonitrile.

Yield: 14 mg (26%) FAB-MS: found: 548 g/mol, calculated; 548.5 g/mol

Examle 54

Solid-phase synthesis of H—IIT—Ala— (IIT—Gly)$_6$—IIT—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 213 mg (0.5 mmol) of IIBocT, 189 mg (1.0 mmol) of tert-butyloxycarbonyl-alanine and 175 mg (1.0 mmol) of tert-butyloxycarbonyl-glycine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 25-minute treatment with a solution of 200 µl of trifluoromethanesulphonic acid in 2 ml of trifluoroacetic acid. Purification is effected by RP-HPLC on C8 using an ascending gradient of TFA in acetonitrile.

Yield: 27 mg (12%) LDI-MS: found: 2178 g/mol, calculated: 2176.1 g/mol

Example 55

Solid-phase synthesis of H—(IIT—Gly—IIT—Asp)$_4$—OH 135 mg (0.1 mmol) of tert-butyl N-fluorenylmethoxycarbonyl-aspartate HMP resin are introduced into the reaction vessel. Prior to each coupling step, the N-fluorenylmethoxycarbonyl protective group is cleaved off by treatment with piperidine. In each case 100 mg (0.2 mmol) of IIFmocT, 297 mg (1.0 mmol) of N-fluorenylmethoxycarbonyl-glycine and 411 mg (1.0 mmol) of tert-butyl N-fluorenylmethoxycarbonyl-aspartate are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the N-fluorenylmethoxycarbonyl protective group is removed by treatment with piperidine. Cleavage from the support is effected by 60-minute treatment with tri-fluoroacetic acid. Purication is effected by RP-HPLC on C8 using an ascending gradient of TFA in acetonitrile.

Yield: 57 mg (24%) LDI-MS: found: 2379 g/mol, calculated: 2380.2 g/mol

Example 56

Solid-phase synthesis of H—Gly—IIIT—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 169 mg (0.5 mmol) of IIIBocT and 175 mg (1.0 mmol) of tert-butyloxycarbonyl-glycine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 60-minute treatment with a solution of 0.5 ml of anisole in 4.5 ml of HF at 0° C. Purification is effected by RP-HPLC on C8 using an ascending gradient of TFA in acetonitrile.

Yield: 15 mg (41%) FAB-MS: found: 367 g/mol, calculated: 367.4 g/mol

Example 57

Solid-phase synthesis of H—IIIT—Gly—IIIT—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 169 mg (0.5 mmol) of IIIBocT and 175 mg (1.0 mmol) of tert-butyloxycarbonyl-glycine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 60-minute treatment with a solution of 0.5 ml of anisole in 4.5 ml of HF at 0° C. Purification is effected by RP-HPLC on C8 using an ascending gradient of TFA in acetonitrile.

Yield: 25 mg (43%) FAB-MS: found: 588 g/mol, calculated: 588.6 g/mol

Example 58

Solid-phase synthesis of H—(IVC)$_2$—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 243 mg (0.5 mmol) of IVBocC$^{Bz}$ are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 8-hour treatment with a solution of 0.5 ml of anisole in 4.5 ml of HF at 0° C. Purification is effected by RP-HPLC on C8 using an ascending gradient of TFA in acetonitrile.

Yield: 33 mg (53%) FAB-MS: found: 616 g/mol, calculated: 617 g/mol

Example 59

Solid-phase synthesis of H—(IIC—Ala)$_2$—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 446 mg (1.0 mmol) of IIBocC$^{Bz}$ and 139 mg (1.0 mmol) of tert-butyloxycarbonyl-alanine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 60-minute treatment with a solution of 0.5 ml of anisole in 4.5 ml of HF at 0° C. Purification is effected by RP-HPLC on C8 using an ascending gradient of TFA in acetonitrile.

Yield: 42 mg (76%) FAB-MS: found: 548 g/mol, calculated: 549.0 g/mol

Example 60

Solid-phase synthesis of H—IVT—IVC—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 198 mg (0.5 mmol) of IVBocT and 243 mg (0.5 mmol) of IVBocC$^{Bz}$ are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 8-hour treatment with a solution of 0.5 ml of anisole in 4.5 ml of HF at 0° C. Purification is effected by RP-HPLC on C8 using an ascending gradient of TFA in acetonitrile.

Yield: 54 mg (86%) ESI-MS: found: 630 g/mol, calculated: 630.6 g/mol ESI: Electron spray ionization Example 61

Solid-phase synthesis of H—Lys—(IVT)$_8$—Ala—OH 125 mg (0.1 mmol ) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 198 mg (0.5 mmol) of IVBocT and 415 mg (1.0 mmol) of tert-butyloxycarbonyl-2-chlorobenzyloxycarbonyl-lysine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxy-carbonyl protective group is removed by treatment with trifluoroacetic acid. Cleavage from the support is effected by 60-minute treatment with a solution of 0.5 ml of anisole in 4.5 ml of HF at 0° C. Purification is effected by RP-HPLC on C8 using an ascending gradient of TFA in acetonitrile.

Yield: 180 mg (74%) ESI-MS: found: 2442 g/mol, calculated: 2443.3 g/mol

Example 62

Solid-phase synthesis of H—Lys—IVT—IVC—IVT—IVC—IVC—IVT—IVC—IVT—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 198 mg (0.5 mmol) of IVBocT, 243 mg (0.5 mmol) of IVBocC$^{Bz}$ and 415 mg (1.0 mmol) of tert-butyloxycarbonyl-2-chlorobenzyloxycarbonyl-lysine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxycarbonyl protective group is removed by treatment with trifluoroacetic acid. Cleavage from the support is effected by 8-hour treatment with a solution of 0.5 ml of anisole in 4.5 ml of HF at 0° C. Purification is effected by RP-HPLC on C8 using an ascending gradient of TFA in acetonitrile.

Yield: 83 mg (35%) LDI-MS: found: 2382 g/mol, calculated: 2383.3 g/mol

Example 63

Solid-phase synthesis of H—Lys—(VT)$_8$—Ala—OH 125 mg (0.1 mmol) of tert-butyloxycarbonyl-alanine-PAM resin are introduced into the reaction vessel. Prior to each coupling step, the tert-butyloxycarbonyl protective group is cleaved off by treatment with trifluoroacetic acid. In each case 115 mg (0.3 mmol) of VBocT and 415 mg (1.0 mmol) of tert-butyloxycarbonyl-2-chlorobenzyloxycarbonyl-lysine are activated by reaction with 135 mg (1.0 mmol) of hydroxybenzotriazole and 206 mg (1.0 mmol) of dicyclohexylcarbodiimide in N-methyl-2-pyrrolidone. Then, the stepwise coupling to the polymeric support takes place. After the last coupling, the tert-butyloxy-carbonyl protective group is removed by treatment with trifluoroacetic acid. Cleavage from the support is effected by 60-minute treatment with a solution of 0.5 ml of anisole in 4.5 ml of HF at 0° C. Purification is effected by RP-HPLC on C8 using an ascending gradient of TFA in acetonitrile.

Yield: 83 mg (35%) LDI-MS: found: 2347.4 g/mol, calculated: 2347.3 g/mol

Demonstration Of Binding To DNA Single Strands Using Gel-Shift Analyses

Example 64

1 μg of oligonucleotide of appropriate base sequence is labelled in a customary manner at the 5' end using polynucleotide kinase and γ-ATP in a volume of 10 μl (Sambrook, Fritsch, Maniatis: Molecular Cloning, A Laboratory Manual, Cold Spring Harbor, 1989). After the labelling, the sample is heated at 70° C. for 10 minutes to denature the enzyme and is subsequently mixed with 9 μg of unlabelled oligomer. A desired quantity of the nucleic acid-binding oligomer being tested (1–10 μg) is added to 1 μl of this mixture and the whole is incubated at 22° C. (room temperature) for 30 minutes in a volume of 20 μl (hybridization). The sample is then placed on ice for 30 minutes. A labelled oligomer which is not hybridized is treated in the same way and serves as the control. The samples are applied to a 15% polyacrylamide gel using 1×Tris-borate-EDTA buffer. The gel and the buffer were precooled in a refrigerator (8° C.), and the electrophoresis was left to run overnight at 55 V in a refrigerator. Following the electrophoresis, an autoradiogram was prepared on AGFA film (exposure times 1 to 16 hours).

Demonstration Of Strand Displacement In Double-Stranded Plasmid DNA By Nucleic Acid-Binding Oligomers Example 65

The tests are carried out as follows:

(The plasmid DNA employed in the example is only a model substrate in the test. Other plasmids which contain poly-adenine sequence regions at defined distances from each other can also be used.)

Double-stranded, circular plasmid DNA, which is 4880 base pairs in length and which contains two poly-adenine sequence regions having at least nine consecutive adenine nucleotides, which sequence regions are at a distance apart of 1150 base pairs, is used in the tests described here.

Six samples, set up in parallel and designated 1–6, each contained 1.0 μg of uncut plasmid DNA in 14 μl of $H_2O$. In each case, 1 μl of solutions of 0.01 μg, 0.1 μg, 1.0 μg and 2.0 μg of nucleic acid-binding oligomers was added to samples 3 to 6, and the mixtures were incubated in sealed Eppendorf reaction tubes at 37° C. for 45 minutes. Subsequently, 4 μl of buffer (250 mM sodium acetate, 1M NaCl, 2.5% of glycerol, 5 mM $ZnCl_2$, pH 4.4) were added to all the samples and 1 μl of S1 nuclease (Aspergillus oryzae, Boehringer-Mannheim), having an activity of 10 U/μl, was added to each of samples 2 to 6.

After having been incubated at 30° C. for 15 minutes, the samples were placed on ice, 1 μl of 0.5M EDTA and 3 μl of loading buffer (50% of glycerol, 0.25% of Bromophenol Blue in 40 mM of Tris-HCl, 20 mM of sodium acetate, 1 mM of EDTA, pH: 7.2) were added, and, without delay, the samples were fractionated electrophoretically on 1.2% agarose gels and, after staining with ethidium bromide, the size of the resulting plasmid fragments in the gel were determined by comparison with a molecular weight standard (1-kb ladder, from Gibco-BRL, D-7514 Eggenstein) on a transilluminator (264 nm UV light).

It was found that DNA fragments of 4880 base pairs (plasmid linearization) and 3730 and 1150 base pairs (sequence-selective fragmentation) were visible in the samples with a concentration of >0.1 μg of oligomer (samples 5 and 6).

Using a modified test batch, in which, instead of the circular plasmid DNA, a plasmid DNA was added to the samples which was linearized by restriction endonuclease digestion in the immediate vicinity of one of the two poly-adenine sequence regions, the DNA fragments of 3730 and 1150 base pairs in length were also detectable in samples 5 and 6.

Using these series of tests, it was possible to demonstrate the concentration-dependent sequence-selective binding of nucleic acid-binding oligomers to double-stranded DNA and to demonstrate the single-stranded DNA, arising as a consequence, by means of S1 nuclease digestion at high salt concentrations (single-strand-specific activity of S1 nuclease).

Inhibition Of Protein Synthesis In In-Vitro Translation Tests By Nucleic Acid-Binding Oligomers Example 66

A rabbit reticulocyte lysate from Promega, Madison, Wisconsin, was used for the in-vitro translation, as were in-vitro transcribed mRNA of the tat gene from HIV-I and of the delta subunit of the acetylcholine receptor from Torpedo californica. Other genes can be used in a similar manner. The cDNA constructs of the genes were transcribed in a customary manner using SP6 RNA polymerase or T7 RNA polymerase (Sambrook et al., ditto), and the DNA plasmid was subsequently digested with DNase, and the mRNA was treated with phenol and precipitated three times with ethanol. 1 to 2 μg of the resulting mRNA were employed for the in-vitro translation in the presence of $^{35}$S-labelled cysteine. The radioactive protein which was formed was analysed on a 6 to 18% or 6–10% discontinuous SDS PAGE by the method of Laemmli, U. K. (1970) Nature 227, 680–685.

In order to measure quantitatively the inhibition of translation by nucleic acid-binding oligomers, a desired quantity of oligomer (0.01 to 2 μg) was added to the mRNA and in vitro translation was then carried out in the rabbit reticulocyte lysate as described above. Autoradiographs of SDS polyacrylamide electrophoresis gels from the test batches were quantitatively evaluated using a scanner.

We claim:

1. A compound of the formula:

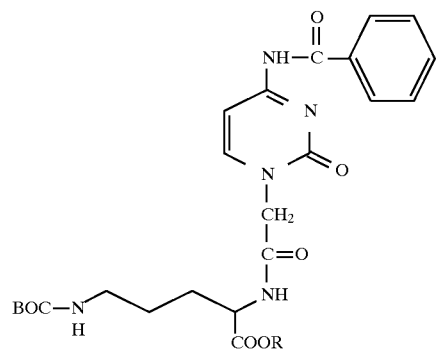

in which

R represents hydrogen or methyl; and

BOC represents tert-butoxycarbonyl;

optionally in the form of a racemic mixture, a stereoisomer mixture, or a purified stereoisomer.

2. A compound of the formula:

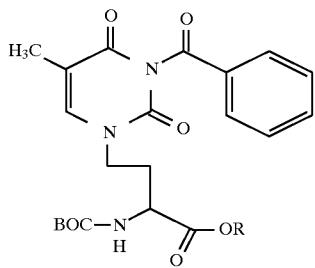

in which

R represents tert-butyl; and

BOC represents tert-butoxycarbonyl;

optionally in the form of a racemic mixture, a stereoisomer mixture, or a purified stereoisomer.

3. A compound of the formula:

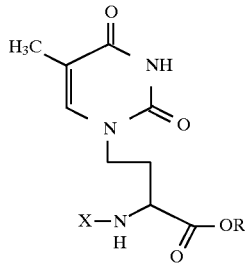

in which

R represents hydrogen or tert-butyl; and

X represents tert-butoxycarbonyl; or

R represents hydrogen; and

X represents 9-fluorenylmenthoxycarbonyl;

optionally in the form of a racemic mixture, a stereoisomer mixture, or a purified stereoisomer.

4. A compound of the formula:

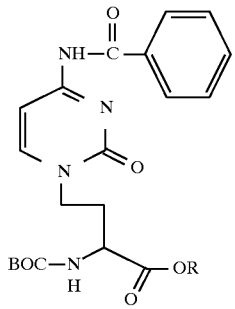

in which

R represents hydrogen; and

BOC represents tert-butoxycarbonyl;

optionally in the form of a racemic mixture, a stereoisomer mixture, or a purified stereoisomer.

5. A compound of the formula:

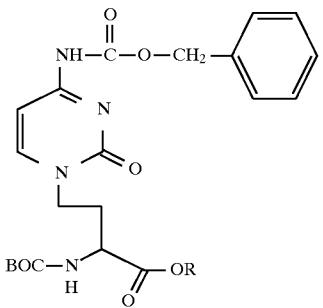

in which

R represents hydrogen or tert-butyl; and

BOC represents tert-butoxycarbonyl;

optionally in the form of a racemic mixture, a stereoisomer mixture, or a purified stereoisomer.

6. A compound of the formula:

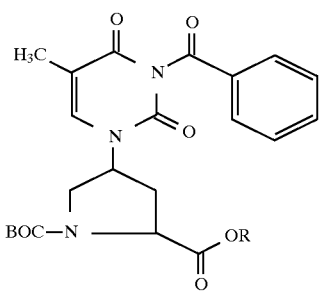

in which

R represents hydrogen, methyl or benzyl; and

BOC represents tert-butoxycarbonyl;

optionally in the form of a racemic mixture, a stereoisomer mixture, or a purified stereoisomer.

7. A compound of the formula:

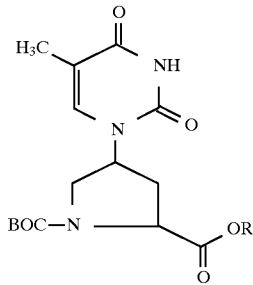

in which

R represents hydrogen; and

BOC represents tert-butoxycarbonyl;

optionally in the form of a racemic mixture, a stereoisomer mixture, or a purified stereoisomer.

8. A compound of the formula:

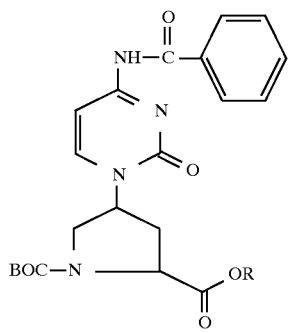

in which
R represents hydrogen or benzyl; and
BOC represents tert-butoxycarbonyl;
optionally in the form of a racemic mixture, a stereoisomer mixture, or a purified stereoisomer.

9. A compound of the formula:

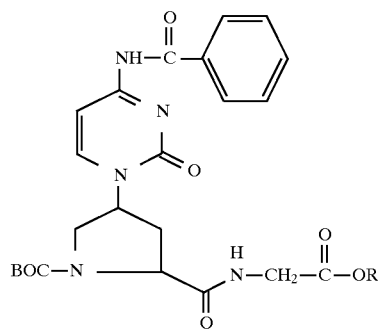

in which
R represents hydrogen or benzyl; and
BOC represents tert-butoxycarbonyl;
optionally in the form of a racemic mixture, a stereoisomer mixture, or a purified stereoisomer.

10. A compound of the formula:

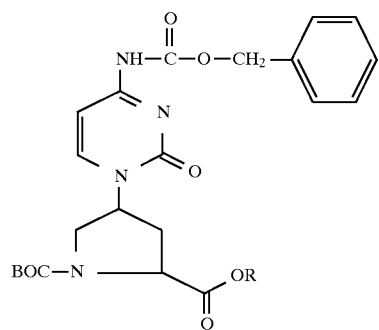

in which
R represents hydrogen or methyl; and
BOC represents tert-butoxycarbonyl;
optionally in the form of a racemic mixture, a stereoisomer mixture, or a purified stereoisomer.

11. A compound of the formula:

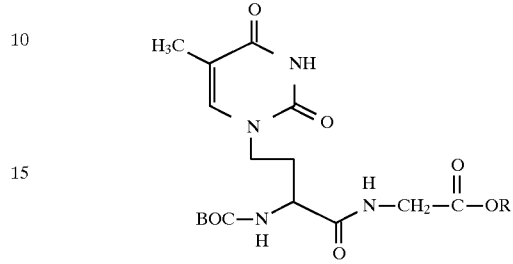

in which

R represents hydrogen or methyl; and
BOC represents tert-butoxycarbonyl;

optionally in the form of a racemic mixture, a stereoisomer mixture, or a purified stereoisomer.

12. A compound of the formula:

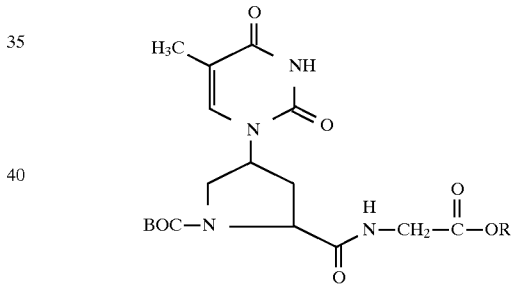

in which

R represents hydrogen or benzyl; and
BOC represents tert-butoxycarbonyl;

optionally in the form of a racemic mixture, a stereoisomer mixture, or a purified stereoisomer.

* * * * *